United States Patent [19]
Barr et al.

[11] Patent Number: 5,624,665
[45] Date of Patent: Apr. 29, 1997

[54] BASIC ALUMINUM ANTIPERSPIRANT ACTIVE MATERIALS HAVING ENHANCED ACTIVITY, ANTIPERSPIRANT ACTIVE COMPOSITIONS CONTAINING SUCH MATERIALS, AND METHODS FOR PREPARATION OF SUCH MATERIALS AND COMPOSITIONS

[75] Inventors: Morton L. Barr, Rockaway; Paul J. Vincenti, Jefferson; Elaine L. Vanderhoof, Long Valley, all of N.J.

[73] Assignee: The Mennen Company, Morristown, N.J.

[21] Appl. No.: 456,482

[22] Filed: Jun. 1, 1995

Related U.S. Application Data

[62] Division of Ser. No. 97,620, Jul. 27, 1993, which is a continuation of Ser. No. 550,683, Jul. 10, 1990, abandoned, which is a continuation-in-part of Ser. No. 518,516, May 2, 1990, Pat. No. 5,202,115, which is a continuation-in-part of Ser. No. 233,008, Aug. 17, 1988, abandoned.

[51] Int. Cl.⁶ .................... A61K 7/38; A61K 7/32; C01F 7/00
[52] U.S. Cl. .................... 424/68; 424/65; 423/600
[58] Field of Search ................... 424/65, 68; 423/600

[56] References Cited

U.S. PATENT DOCUMENTS 5,202,115  4/1993  Vincenti et al. .................... 424/66

*Primary Examiner*—Shelley A. Dodson
*Attorney, Agent, or Firm*—Antonelli, Terry, Stout & Kraus, LLP

[57] ABSTRACT

Disclosed are basic aluminum antiperspirant materials having univalent complex oxoanions (e.g., nitrate); methods of making such materials; antiperspirant compositions containing such basic aluminum materials, another antiperspirant active material (e.g., a basic zirconium halide salt), and optionally a neutral amino acid; and methods of making such compositions. Size exclusion high performance liquid chromatography chromatograms of the disclosed basic aluminum materials have a peak 4 relative area of at least 25%, a peak 3 relative area of less than 60%, the sum of the peaks 3 and 4 being at least 50%; and less than 10% of the chromatographic peaks eluting at peaks 1 and 2. The disclosed basic aluminum materials have less than 25% of the aluminum in the form of $Al^b$ polyhydroxyaquoaluminum, and have a $^{27}Al$ NMR spectrum in which the area of the 71.5–73.5 ppm resonance line includes more than 50% of the combined areas of the 62.5–63.5 ppm and 71.5–73.5 ppm resonance lines, and 5%–30% of the total area under the spectrum from 140 ppm to −80 ppm is contained in the resonance line at 71.5–73.5 ppm. The basic aluminum material of the present invention can be produced by adding a stoichiometric or near-stoichiometric amount of aluminum metal to a solution of an aluminum salt having a univalent complex oxoanion; the basic aluminum material can also be made by adding to such solution of the aluminum salt, aluminum metal having, in total, a relatively small surface area (large-sized particles of aluminum).

31 Claims, 11 Drawing Sheets

BASIC ALUMINUM ANTIPERSPIRANT ACTIVE MATERIALS HAVING ENHANCED ACTIVITY, ANTIPERSPIRANT ACTIVE COMPOSITIONS CONTAINING SUCH MATERIALS, AND METHODS FOR PREPARATION OF SUCH MATERIALS AND COMPOSITIONS

This application is a Divisional application of application Ser. No. 08/097,620, filed Jul. 27, 1993, abandoned, which is a Continuing application of application Ser. No. 07/550,683 filed Jul. 10, 1990, abandoned, which is a Continuation-in-Part application of application Ser. No. 07/518,516, filed May 2, 1990, U.S. Pat. No. 5,202,115, which is a Continuation-in-Part application of application Ser. No. 07/233,008, filed Aug. 17, 1988, abandoned.

BACKGROUND OF THE INVENTION

The present invention relates to basic aluminum antiperspirant active materials containing univalent complex oxoanions, antiperspirant active compositions including such basic aluminum antiperspirant active materials and also containing another antiperspirant active salt such as a zirconium, hafnium, titanium and/or tin salt, and methods for producing such materials and compositions. The materials and compositions of the present invention have a wide range of application as antiperspirant materials, including, for example, as antiperspirant active agents in aerosols, roll-ons, solid sticks, and other known systems for delivery of antiperspirant materials to, e.g., the axillary region of the human body.

The present invention is particularly directed to basic aluminum antiperspirant materials containing a univalent complex oxoanion of nitrogen or halogen, antiperspirant compositions containing such materials, and methods of making such materials and such compositions.

In conventional basic aluminum halides, including those having enhanced activity, aluminum metal has been added in excess to a solution of the aluminum halide salt, since it is known in the art that the formation of conventional basic aluminum halides requires a level of aluminum metal, to be added to a solution of monomeric aluminum halide, that is in excess of that required by reaction stoichiometry. According to Fitzgerald, "Chemistry of Basic Commercial Aluminum Hydrolysis Complexes" in Laden, et al, *Antiperspirants and Deodorants* (1988), page 219, aluminum metal is added in a two—to four—fold excess. If aluminum metal is not added in such excess, aluminum metal will not solubilize rapidly, the aquated aluminum ions will not hydrolyze sufficiently nor achieve a sufficiently high level of aggregation, and the desired end product will not be formed within a commercially feasible time frame. Aluminum metal may be added in stoichiometric excess in order to ensure a large aluminum metal surface area for more rapid dissolution of the required amount of metal into water. Once aluminum metal is oxidized by acidic water, the resultant aquated $Al^{3+}$ is available to hydrolyze and form larger hydroxyaquoaluminum aggregates.

The reason for adding such stoichiometric excess of aluminum metal, in forming conventional basic aluminum halide materials, can be seen in the following. The reaction stoichiometry for formation of conventional basic aluminum halides can be described by the following reactions:

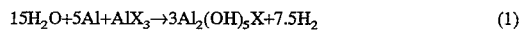  (1)

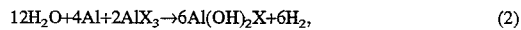  (2)

where X is a halide.

It can be seen that in reaction (1), the aluminum metal to aluminum halide molar ratio is 5:1, and in reaction (2) such molar ratio is 2:1. Reaction equations (1) and (2) represent extremes in commercial basic aluminum halides. As can be seen, the aluminum metal to aluminum halide molar ratio determines what the end product can theoretically be. The rate of aluminum metal dissolution into water strongly influences what the end product actually will be. In each case, in order to ensure formation of the desired end product within a commercially feasible time frame, the actual aluminum metal to aluminum halide molar ratio used commercially is larger than that required by the reaction stoichiometry represented by the above reaction equations. Typically, this molar ratio of actual aluminum metal to aluminum halide, in commercial systems, will vary between 3:1 and 10:1.

As can be seen in the foregoing, the important feature in forming conventional basic aluminum halide material is to achieve rapid solubilization of the aluminum metal (as discussed in the above, for example, by adding a level of aluminum metal in excess of that required by reaction stoichiometry). Larger aluminum metal surface areas, for example, by use of aluminum powders, would also permit achievement of relatively rapid solubilization of the aluminum. Thus, for example, use of aluminum powders would permit use of lower molar ratios. Unfortunately, aluminum metal powder is hazardous to handle, and can be explosive if proper precautions are not taken.

U.S. patent application Ser. No. 07/518,516, filed May 2, 1990, now U.S. Pat. No. 5,202,115, issued Apr. 13, 1993 which is a continuation-in-part application of U.S. patent application Ser. No. 07/233,008, filed Aug. 17, 1988 (the contents of the continuation-in-part application and the contents of No. 07/233,008 each being incorporated herein in their entirety), discloses basic aluminum antiperspirant active materials (polymeric aluminum materials) having the empirical formula: $Al_2(OH)_{6-a}X_a$, where $0.5 \leq a \leq 5.0$, and X is a univalent complex oxoanion of nitrogen or halogen, such as $NO_3^-$, $ClO_3^-$, $ClO_4^-$ and $IO_4^-$, the antiperspirant active material being further characterized by:

(a) Size exclusion high performance liquid chromatography (HPLC) peaks corresponding to peak 3 and peak 4 of the size exclusion chromatogram produced from a high performance liquid chromatography technique;

(b) A peak 4 relative area of at least 25%, and a peak 3 relative area of less than 60%, the sum of the relative peak 3 and peak 4 areas being at least 50%; and (c) Less than 10% chromatographic peaks eluting at shorter retention times (or larger molecular sizes) than the peak 3, corresponding to peaks 1 and 2.

This continuation-in-part application discloses that the basic aluminum materials described therein can be produced at relatively low temperatures, such as at temperatures below 45° C., with the time of heating in the temperature range of 45° C.–140° C. being 0.5–17 hours. This continuation-in-part application discloses that the basic aluminum materials described therein can be formed at lower temperatures, and/or in smaller amounts of time, and at higher initial aluminum solution concentrations, than when using techniques for forming conventional basic aluminum halide materials having enhanced antiperspirant activity.

This continuation-in-part application discloses that the described basic aluminum material can be formed by dissolving an aluminum salt of the univalent complex oxoanion in water, heating, and (while heating) adding additional aluminum in metallic form. Where the aluminum salt is an aluminum nitrate, the reaction scheme for forming the basic aluminum material in the foregoing continuation-in-part application is described as follows:

$$58H_2O+28Al+16Al(NO_3)_3 \rightarrow 22Al_2(OH)_5NO_3+26NO+3H_2,$$

where the production of nitric oxide represents a reduction of the nitrate oxoanion from a formal +7 to +2 oxidation state on the nitrogen atom. This continuation-in-part application also discloses that the aluminum salt of the univalent complex oxoanion can be formed in situ, by reacting aluminum metal with, e.g., an inorganic acid of the univalent complex oxoanion.

Consistent with techniques in connection with conventional basic aluminum halide materials, this continuation-in-part application describes forming the described basic aluminum material having the univalent complex oxoanion by adding small turnings of aluminum metal in the form of oblong pieces 1/16 inch to 1/8 inch long and 1/100 inch to 3/100 inch thick, in excess, to a solution of monomeric aluminum ion and univalent complex oxoanion.

This continuation-in-part application also discloses a basic aluminum antiperspirant material having enhanced efficacy, wherein such material contains at least 25% by weight of the aluminum in the form of $Al^b$ polyhydroxyaquoaluminum. This continuation-in-part application discloses that, typically, the antiperspirant active material contains up to 50% by weight of the total aluminum in the form of $Al^b$polyhydroxyaquoaluminum.

While the continuation-in-part application, and application Ser. No. 07/233,008, describe basic aluminum antiperspirant materials containing univalent complex oxoanions, having enhanced antiperspirant activity, which can be provided directly (that is, without previously forming a basic aluminum material and then heating) at relatively low temperatures and which are relatively stable, it is still desired to provide basic aluminum materials having improved antiperspirant activity and which can be provided utilizing a relatively safe and inexpensive technique, in a relatively short period of time.

U.K. Patent Application No. 2,048,229 describes a group of complexes ($Al^{c'}$) within the aluminum chlorhydroxides which are more efficacious as an antiperspirant. Such group $Al^{c'}$ complexes with a ferron reagent at a reaction rate characteristic of $Al^c$ (of $Al^a$, $Al^b$ and $Al^c$, $Al^c$ is the group that exhibits the slowest complexing reaction ratio with ferron), and has a permeation rate in gel permeation chromatography which is within that range generally found for $Al^b$ (of $Al^a$, $Al^b$ and $Al^c$, $Al^b$ has an intermediate retention time, indicating it includes complexes of intermediate molecular size). This U.K. patent application describes that the $Al^{c'}$ group of complexes was present in amounts of 10%–30% by weight in then-available aluminum chlorhydroxides, and that these then-available aluminum chlorhydroxides can be modified to contain substantially larger amounts of the $Al^{c'}$ group. This patent application discloses a technique to increase the amount of the $Al^{c'}$ group, by aging then available (commercial) aluminum chlorhydroxide.

This U.K. Patent Application does not disclose use of basic aluminum materials having a univalent complex oxoanion of nitrogen or a halogen, does not describe direct preparation of the basic aluminum material (rather, disclosing aging of then available aluminum chlorhydroxide), and does not achieve the advantages of the present invention.

European Patent Application No. 191,628, the contents of which are incorporated herein by reference in their entirety, discloses a direct process of making a basic aluminum halide in powder form having an aluminum:halogen molar ratio of from 1.7 to 2.2:1 and having at least 20% of the aluminum contained in a Band III fraction. This process includes steps of:

(a) dissolving metallic aluminum in an aqueous starting solution of an aluminum compound selected from aluminum chloride and aluminum bromide, the starting solution being held at a temperature of about 50° C. to about 105° C., for a time just long enough to dissolve sufficient aluminum to produce an aqueous solution of a final basic aluminum halide having an aluminum:halide molar ratio in the range 1.7:1 to 2.2:1, the concentration of the aluminum in the starting solution and the amount of aluminum dissolved being such that the aluminum concentration in the solution of the final basic aluminum halide is from 0.8% to 6.75% by weight, and the final basic aluminum halide having at least 20% of the aluminum contained in the Band III fraction; and (b) drying the solution of the final basic aluminum halide so as to give the final basic aluminum halide in the form of a hydrated powder having at least 20% of the aluminum contained in the Band III fraction.

European Patent Application No. 191,628 further discloses that in the direct preparative procedure for forming the described basic aluminum halide material, under some conditions products containing a high proportion of the aluminum in the Band III species contain a substantial proportion of this component in the form of a polymer having a characteristic line in the $^{27}Al$ NMR (nuclear magnetic resonance) spectrum. This patent application discloses this characteristic line is 62.5 ppm downfield from the resonance of $Al^{3+}(6H_2O)$, and has been attributed to a complex aluminum ion referred to as the $Al_{13}O_{40}$ ion. In one embodiment of the disclosed process, at least 20% of the aluminum of the final basic aluminum compound is in the form of the $Al_{13}O_{40}$ ion.

European Patent Application No. 285,282 discloses antiperspirant materials, including partially neutralized aluminum salts, the salts having at least 25% of the total aluminum present in a form having a $^{27}Al$ NMR spectrum wherein 8% to 25% of the total area under the spectrum from 140 ppm to −80 ppm is contained in a peak at approximately 63 ppm (corresponding to tetrahedrally co-ordinated aluminum ions). This European patent document discloses a technique for forming the described aluminum salt, by partially neutralizing an aqueous acid (such as a mineral acid) using a source of aluminate ion (the mineral acid optionally being an aluminum salt), with no subsequent heating step required. Specifically embodied in this patent document are aluminum halohydrate materials, such as aluminum chlorhydrate; the disclosed aluminum chlorhydrate has an increased proportion of smaller species and is deficient in the larger polymeric species.

While each of European Patent Application No. 191,628 and No. 285,282 describe direct techniques for forming a basic aluminum antiperspirant material, each of these patent documents are primarily directed to halide materials. Moreover, European Patent Application No. 285,282 discloses halide and nitrate materials formed by reacting an aluminate with, e.g., an aluminum salt, rather than use of aluminum metal to react with an aluminum salt. Neither of these European patent applications disclose basic aluminum compounds as in the present invention, having enhanced antiperspirant activity, which can be manufactured by a relatively safe and inexpensive technique.

It is also desired to provide an antiperspirant composition including a basic aluminum material containing a univalent complex oxoanion and another antiperspirant active material, and a method of producing such composition.

The aforementioned continuation-in-part U.S. patent application, filed May 2, 1990, and its parent application Ser. No. 07/233,008, filed Aug. 17, 1988 (the contents of each of which have previously been incorporated herein by reference in their entirety) disclose incorporating the described basic aluminum antiperspirant material with enhanced antiperspirant activity, having a univalent complex oxoanion, in a composition including another antiperspirant active compound (for example, a compound containing a metal cation selected from Zr, Hf, Ti or Sn), such composition containing (or not containing) a neutral amino acid. The patent applications disclose that the composition can be prepared by simple mixing of a solution of the basic aluminum material having enhanced antiperspirant activity with a solution of the Zr, Hf, Ti and/or Sn material (for example, a solution of zirconyl hydroxychloride), the temperature of such mixing being at least room temperature, and, illustratively, at a temperature of 45°–140° C. The patent applications disclose that the composition can be provided without dilution and/or heating, and thus is more stable in water as compared to corresponding compositions using aluminum chlorhydrate of enhanced antiperspirant activity.

U.S. Pat. No. 2,814,585 to Daley discloses an antiperspirant composition including in combination an aqueous solution of a zirconium or hafnium salt of a strong monobasic mineral acid, a basic aluminum compound, and an amino acid in which the number of amino groups is equal to the number of carboxyl groups in the molecule (that is, neutral amino acids). This patent discloses that the basic aluminum compounds and the amino acids act as buffering agents to bring the pH of the solution of the zirconium or hafnium salt to a value which renders it safe for antiperspirant usage. This patent discloses that the basic aluminum compounds with which the hafnium and zirconium salts, and neutral amino acids, are combined have the general empirical formula $Al_2(OH)_{6-n}X_n$, where X is a monovalent acid anion of the group $Cl^-$, $Br^-$, $I^-$ and $NO_3^-$, and n has an average value from about 0.8 to about 2.

U.S. Pat. No. 4,331,609 to Orr discloses antiperspirant compositions which are non-irritating to the skin and which are non-damaging to textiles, the compositions including an aluminum compound, a zirconium compound, a neutral amino acid and an inorganic acidic compound. This patent discloses that the aluminum compound has the empirical formula $Al_2(OH)_{6-n}X_n$, wherein n has a value of from about 0.80 to about 1.25 and X is selected from the group consisting of chlorine, bromine, iodine, sulfamate, sulfate, nitrate and mixtures thereof.

While each of U.S. Pat. No. 2,814,585 and 4,331,609 disclose antiperspirant compositions including a basic aluminum compound containing a univalent complex oxoanion (e.g., nitrate), neither of these patents disclose that the basic aluminum nitrate is a nitrate having enhanced antiperspirant activity, much less compounds having specific NMR spectra and/or form. Moreover, these patents do not disclose achieving further enhanced activity, based on specific techniques for forming the compounds. In addition, these patents teach that the nitrates therein are equivalent to, e.g., the chlorides.

U.S. Pat. No. 4,775,528 to Callaghan, et al discloses an antiperspirant composition having high antiperspirant efficacy, comprising zirconyl hydroxychloride and aluminum chlorhydroxide in which the atomic ratio of Al to Zr is from 6:1 to 1:1, such composition (when dissolved in water to form a 10% by weight solution and, after storage at room temperature for no more than two hours, subjected to gel permeation chromatography on cross-linked dextran having a molecular weight exclusion range of 1,000 to 30,000 for globular proteins (Sephadex G-50)) exhibiting a distribution pattern having peaks at Kd=0.7 and Kd=0.5 in which the ratio of the height of the first peak to that of the second is at least 1.5:1. This patent also discloses a method of making such composition, wherein a 2%–18% solution of aluminum chlorhydroxide in water is heated at a temperature of at least 50° C. with the zirconyl hydroxychloride being mixed therewith before, during or after the heating step, the amount of the zirconyl compound being sufficient to provide an atomic ratio of Al:Zr from 6:1 to 1:1, the heating being continued until the above-referred-to distribution pattern is achieved. This patent further discloses that the composition can optionally also include a neutral amino acid. With reference to FIG. 1 of U.S. Pat. No. 4,775,528, this patent teaches that peak 1 of the chromatogram of the composition (peak 1 being the first eluted fraction) contains the zirconium compound; that peak 2 contains the $Al^c$ complex; that peak 3, at Kd=0.5, contains the $Al^{c'}$ complex; and that peak 4, at Kd=0.7, which appears only as a shoulder between peaks 3 and 5, contains a hitherto unrecognized novel complex which is present only in a small proportion, while peaks 5 and 6 are fractions containing $Al^a$ or other lower molecular weight compounds.

This patent does not teach or suggest compositions including basic aluminum materials, having enhanced antiperspirant activity, containing univalent complex oxoanions, as in the present invention. Moreover, this patent does not teach or suggest the amount of the basic aluminum compound in the form of $Al^b$, or the $^{27}Al$ NMR spectrum, as in the present invention.

U.S. Pat. No. 4,606,915 to Rosenberg, et al discloses that a composition of a stannic halide and an aluminum halohydrate, and also preferably containing a neutral amino acid, is useful in inhibiting perspiration when applied to the skin of a subject in powder form or when incorporated in a liquid or solid vehicle. In this patent, there is no disclosure that the aluminum compound has enhanced activity, nor that the resultant basic tin/aluminum halohydrate demonstrates enhanced antiperspirant activity. The contents of U.S. Pat. No. 4,606,915 are incorporated herein by reference in their entirety.

Accordingly, it is still desired to provide basic aluminum materials with further enhanced antiperspirant activity; and compositions of (1) zirconium, hafnium, tin and/or titanium active antiperspirant material, either those conventionally known or those having enhanced antiperspirant activity, with (2) basic aluminum material having further enhanced antiperspirant activity, which materials and compositions can be made inexpensively and safely, and which are stable after being formed. It is also desired to make such basic aluminum materials and such compositions, without the necessity of using high temperatures and/or high pressures, and without the need for extra manufacturing steps of heating diluted solutions of already manufactured basic aluminum compounds. It is also desired to provide such materials and compositions in concentrated aqueous solutions.

SUMMARY OF THE INVENTION

Accordingly, it is an object of the present invention to provide basic aluminum antiperspirant active materials (containing, e.g., univalent complex oxoanions) having further enhanced antiperspirant activity, which can be produced relatively cheaply and safely (for example, with substantially decreased danger of explosion), and to provide methods of making such materials.

It is another object of the present invention to provide antiperspirant compositions containing (1) such basic aluminum antiperspirant active materials having further enhanced antiperspirant activity, and (2) at least another antiperspirant active material such as another antiperspirant active salt, and methods of making such compositions.

It is a further object of the present invention to provide such basic aluminum materials, which can be produced at relatively low temperatures and fast rates, with a higher initial aluminum concentration in the solution.

It is a still further object of the present invention to provide such basic aluminum antiperspirant active materials with further enhanced activity, and methods of forming such materials, wherein the materials can be provided without the need for extra manufacturing steps of heating diluted solutions of already manufactured basic aluminum materials at high temperature and/or pressure conditions.

It is a still further object of the present invention to provide such basic aluminum antiperspirant materials having further enhanced antiperspirant activity, which has improved stability in aqueous solution over extended periods of time.

It is a still further object of the present invention to provide antiperspirant compositions having further enhanced antiperspirant activity, the compositions including basic aluminum antiperspirant materials having further enhanced antiperspirant activity together with another antiperspirant active material, which has improved stability in aqueous solution and which can be produced at lower temperatures, and methods of producing such compositions.

The present invention achieves each of the above objectives with basic aluminum materials (polymeric aluminum materials) having the empirical formula:

$$Al_2(OH)_{6-a}X_a,$$

where $0.5 \leq a \leq 5.0$, X is an anion as discussed further infra, and wherein the antiperspirant active material is further characterized by:

(a) size exclusion high performance liquid chromatography peaks corresponding to peak 3 and peak 4 of the size exclusion chromatogram produced from a high performance liquid chromatography (HPLC) technique, discussed further infra:

(b) a peak 4 relative area of at least 25%, and a peak 3 relative area of less than 60%, the sum of the relative peak 3 and peak 4 areas being at least 50%;

(c) less than 10% chromatographic peaks eluting at shorter retention times (or larger molecular sizes) than peak 3, corresponding to peaks 1 and 2;

(d) less than 25% of the aluminum being in the form of $Al^b$ polyhydroxyaquoaluminum;

(e) an $^{27}Al$ NMR (nuclear magnetic resonance) spectrum wherein 5%–30%, preferably 8%–18%, of the total area under the spectrum from 140 ppm to −80 ppm is contained in a resonance line at 71.5–73.5 ppm; and (f) an $^{27}Al$ NMR spectrum in which the area of the 71.5–73.5 ppm resonance line includes more than 50% of the combined areas of the 62.5–63.5 ppm and 71.5–73.5 ppm resonance lines.

The anions (X) of the above-stated empirical formula, within the scope of the present invention, are univalent complex oxoanions of nitrogen, chlorine and other halogens, including, but not limited to, $NO_3^-$, $ClO_3^-$, $ClO_4^-$ and $IO_4^-$, which form salts with $Al^{3+}$ in aqueous solution, so that these salts are essentially completely dissociated, which anions are readily soluble in water with metallic ions in the solution (for example, Al ions; or, where the solution contains other antiperspirant active materials such as Zr, Hf, Ti and/or Sn antiperspirant active materials, Al ions and the metallic ions of the other antiperspirant materials), and which form conjugate acids that are strong acids. By strong acid, we mean those acids having the ability to substantially completely dissociate $H^+$ (e.g., at least 98% dissociated) in aqueous solution. Furthermore, those anions within the scope of the present invention are labile with respect to undergoing reduction, the products of the reduction being gases or soluble anions of lower oxidation states of nitrogen or halogen than in the starting anion (the starting anion is the anion of the Al salt used to form the basic aluminum material of the present invention, as discussed further infra). A preferred anion is the nitrate anion ($NO_3^-$).

Various anions which can be utilized as part of the present invention have been set forth above, as well as functional characteristics of usable anions in general. Sulfate and phosphate anions (and similar anions) will not work as part of the present invention, because they complex to too great an extent with aluminum.

The basic aluminum materials of the present invention have substantially no species with a size greater than 100Å. Furthermore, the pH of the basic aluminum materials within the scope of the present invention is higher than that of the corresponding basic aluminum halide material; thus, materials within the scope of the present invention are gentler on the skin of axillary areas, as compared to the corresponding basic aluminum halide materials.

Preferred relative areas for peak 3 and peak 4 of the basic aluminum material are a peak 4 area of at least 35% but less than 80% and a peak 3 area of less than 50%, the sum of the peak 3 and peak 4 areas being at least 60% but less than 90%; moreover, it is also preferred that the basic aluminum material include essentially no peaks 1 and 2.

The foregoing objectives can also be achieved by the process of the present invention, wherein aluminum metal is added to a solution of an aluminum salt in such a manner as to achieve a low aluminum metal surface area, rather than to achieve a large metal surface area as is necessary in forming basic aluminum halides of the prior art.

Methods of forming the basic aluminum materials of the present invention involve dissolving an aluminum salt of the aforementioned univalent complex oxoanions in water, heating, and (while heating) adding additional aluminum in the metallic form. In general, the reaction can be written as follows:

$$H_2O+Al+Al(Y^wO_n)_3 \rightarrow Al_2(OH)_{6-a}(Y^zO_n)_a+H_2+(Y_p{'}O_h)^f,$$

where a is as defined previously, $Y^zO_n$ is a univalent complex oxoanion of nitrogen or halogen described previously as X, p is 1 or 2, $0 \leq h \leq 5$, w is the oxidation state of nitrogen or halogen, n is dependent upon the oxidation state of Y, f is 0 or −1, $0 \leq v < w$ and $0 < z \leq w$. The relationship between w and v represents an overall reduction of the Y atom resulting in a lower oxidation state for that atom in the $Y_p{'}O_h$ by-product than in the original $Al(Y^wO_n)_3$. As is clear from the foregoing reaction scheme, the anion of the aluminum salt reactant is labile with respect to undergoing reduction. Moreover, as indicated previously, the product of the reduction ($Y_p{'}O_h$) is a gas or soluble substance.

In the foregoing reaction scheme, the Al is added, according to the present invention, to achieve a low aluminum metal surface area. Adding the aluminum metal to the solution of the aluminum salt, the aluminum metal dissolves rapidly in water, the aquated aluminum ion hydrolyzes sufficiently and achieves a sufficiently high level of aggregation, and the reaction easily and quickly goes to completion in a commercially feasible time frame.

Furthermore, lowering the aluminum metal surface area allows greater control over the course and extent of the oxidation-reduction-hydrolysis reaction. That is, using the method of the present invention it is easier to isolate a basic aluminum material with any desired distribution of polyhydroxyaquoaluminum polymer sizes according to size exclusion HPLC.

Another advantage of the present methods for forming the basic aluminum materials according to the present invention, utilizing aluminum metal so as to achieve a low aluminum metal surface area, is the fact that it is unnecessary to use hazardous powdered aluminum metal (for providing a large metal surface area as is necessary in basic aluminum halides of the prior art) in order to achieve lower aluminum metal molar ratios and/or faster reaction rates.

Thus, according to the present methods, the aluminum is added in such a manner as to achieve a low aluminum metal surface area, such that the resultant basic aluminum material contains significantly less aluminum in the form of $Al^b$ polyhydroxyaquoaluminum, less aluminum in the form of polymers characterized by an $^{27}Al$ NMR resonance line at 62.5–63.5 ppm, and significantly more aluminum in the form of polymers characterized by a $^{27}Al$ NMR resonance line at 71.5–73.5 ppm than obtained when aluminum metal is added in such a way as to ensure a large metal surface area.

As another way of defining a preferred aspect of the methods according to the present invention, aluminum metal is added to a solution of the aluminum salt so as to achieve a low aluminum metal surface area such that the formed basic aluminum material has less than 25% of the aluminum in the form of $Al^b$ polyhydroxyaquoaluminum and has a $^{27}Al$ NMR spectrum in which the area of the 71.5–73.5 ppm resonance line comprises more than 50% of the combined areas of the 62.5–63.5 ppm and 71.5–73.5 ppm resonance lines.

Desirably, the formed basic aluminum materials have an $^{27}Al$ NMR spectrum wherein 5%–30%, preferably 8%–18%, of the total area under the spectrum from 140 ppm to −80 ppm is contained in a resonance line at 71.5–73.5 ppm.

In the foregoing description concerning the methods of forming the basic aluminum material, it is described that the aluminum salt of the univalent complex oxoanion (Al($Y'''O_n$)$_3$) is dissolved in water, with additional aluminum being added (while heating). However, the formation of the basic aluminum material of the present invention can be practiced by the preparation of the aluminum salt of the univalent complex oxoanion in situ, by mixing aluminum metal with an inorganic acid, $HY'''O_n$; permitting the aluminum metal to dissolve (heating is usually necessary, typically between 45°–140° C.); and then continuing the reaction by addition of more aluminum metal to the formed Al($Y'''O_n$)$_3$ as discussed in the foregoing. The aluminum metal mixed with the inorganic acid may be of large or small surface area. The acid utilized in the in situ formation of Al($Y'''O_n$)$_3$ can be illustratively (but not limitingly), $HNO_3$, $HClO_4$, $HClO_3$ and $HIO_4$. In forming the nitrate, $HNO_3$ is used.

The present invention also includes incorporating the basic aluminum antiperspirant materials as described above, having the recited $Al^b$ polyhydroxyaquoaluminum amount and $^{27}Al$ NMR spectrum, with another antiperspirant active material (e.g., an antiperspirant active salt of Zr, Hf, Ti or Sn), and with or without a neutral amino acid, to form antiperspirant compositions. Specifically, the antiperspirant compositions can be the following:

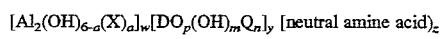 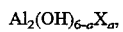

where a and X are as defined previously, w:y ranges from about 0.3:1 to about 6.0:1, z:y ranges from 0 to 1.3:1 and p is either 0.0 or 1.0. When p=0, then m=0 and n=4; when p=1, then m+n=2. While not limiting, D illustratively is a metal cation selected from Zr, Hf, Ti or Sn; and Q is a halide, such as Cl, $NO_3$ or any of the univalent complex oxoanions further described herein. Generally, the compound containing the metal cation selected from Zr, Hf, Ti or Sn includes those known as active antiperspirant materials, and which are compatible with the basic aluminum material of the present invention. The preferred neutral amino acid is glycine, but may be alanine, phenylalanine or other known neutral amino acids.

The compositions according to the present invention have a peak 4 relative area of at least 25%, and a peak 3 relative area of less than 50%, the sum of the peak 3 and peak 4 areas being at least 40%. Unlike the basic aluminum antiperspirant material, the active composition of the present invention, containing a zirconium compound component, for example, may contain significantly more than 10% chromatographic peaks eluting at shorter retention times than peak 3, corresponding to peak 1 and not peak 2, said composition having less than 10% chromatographic peaks corresponding to peak 2. For example, the zirconium compound component could contribute more than 10% peak 1 to the active composition. The active composition of the present invention may contain up to 35% chromatographic peak 1 corresponding to the zirconium compound component of the composition.

The compositions can be prepared by simple mixing of a solution of the basic aluminum material having the enhanced antiperspirant activity, with a solution of the metal cation compound (for example, a solution of zirconyl hydroxychloride). The temperature of such mixing can be at least room temperature, for example, at room temperature. The mixing can be at temperatures above room temperatures, for example, at temperatures of 45° C.–140° C.

The basic aluminum antiperspirant materials of the present invention, and the compositions of the present invention including such basic aluminum materials, can be obtained in powdered form from an aqueous solution by spray-drying or freeze-drying, for example. The conversion of the aqueous antiperspirant solution to a dried (for example, spray-dried) antiperspirant powder can be accomplished by any one of many techniques known to those skilled in the art, and these techniques are more or less suitable for commercial use.

As another aspect of the present invention, the aluminum metal should be added in stoichiometric or near-stoichiometric amounts to a solution of Al($Y'''O_n$)$_3$, where Y, w and n are defined as set forth previously, rather than in excess as in prior techniques. Using such stoichiometric or near-stoichiometric amounts of aluminum, the reaction easily and quickly goes to completion, the aluminum hydrolyzing sufficiently and achieving a sufficiently high level of aggregation. Moreover, when the aluminum metal is added in stoichiometric amounts, the resultant basic aluminum material contains significantly less $Al^b$ polyhydroxyaquoaluminum and less aluminum in the form of polymers characterized by a $^{27}Al$ NMR resonance line at 62.5–63.5 ppm than obtained when aluminum metal is added in large excess.

As a further aspect of the basic aluminum materials of the present invention is basic aluminum materials (polymeric aluminum materials) having the empirical formula:

$$Al_2(OH)_{6-a}X_a,$$

where a and X are as defined previously, with the antiperspirant active material being further characterized by:

(a) a size exclusion HPLC chromatogram which contains:
(1) a peak 4 relative area of at least 40%, a peak 3 relative area of less than 30%, the slim of the relative peak 3 and peak 4 areas being at least 50%;
(2) a combined peak 5 and 6 relative area of at least 15%; and
(3) less than 10% chromatographic peaks eluting at shorter retention times than peak 3, corresponding to peaks 1 and 2;
(b) a $^{27}$Al NMR spectrum in which:
(1) a 71.5–73.5 ppm resonance line comprises at least 5% of the total area of the NMR spectrum, and desirably can comprise as much as 30% of the total area;
(2) a 0–5 ppm resonance line comprises at least 5% of the total NMR area, and desirably can comprise as much as 30% of the total area; and
(3) a 62.5–63.5 ppm resonance line comprises less than 10% of the total area of the NMR spectrum; and
(c) less than 25% of the total aluminum in the form of $Al^b$ polyhydroxyaquoaluminum.

As another aspect of the present invention, the basic aluminum materials described above, which can be formed by adding the aluminum metal in stoichiometric amounts, can be reacted for an additional period of time sufficient to maximize the HPLC peak 4 relative area of the basic aluminum materials to at least 60%, while maintaining a peak 3 relative area of less than 25%, with the sum of peak 3 and peak 4 being at least 70%, and the combined peak 5 and peak 6 area being less than 20%. This aspect of the basic aluminum material is further characterized by an $^{27}$Al NMR spectrum 0–5 ppm resonance line of less than 10% of the total area. Other characteristics of this aspect of the present invention (the amounts of peaks corresponding to peaks 1 and 2, the 71.5–73.5 and 62.5–63.5 ppm resonance lines, and the $Al^b$ polyhydroxyaquoaluminum) are the same as set forth in the immediately preceding paragraph.

Accordingly, the present invention achieves antiperspirant active materials, and compositions containing such active materials, having enhanced antiperspirant activity that is even further enhanced than the antiperspirant activity of the compounds and compositions described in U.S. patent application Ser. No. 233,008, and the continuation-in-part application thereof. Moreover, the present materials and compositions can be provided using relatively large pieces of aluminum, avoiding any possibility of hazards of explosion due to use of, e.g., aluminum metal powder. Furthermore, through use of near-stoichiometric amounts of aluminum, excess use of aluminum can be avoided so that costs due to such excess aluminum can be avoided. In addition, the present invention also achieves all advantages achieved by the material and composition described in U.S. patent application No. 233,008, and the continuation-in-part application thereof.

DETAILED DESCRIPTION OF THE INVENTION

Figure 1:
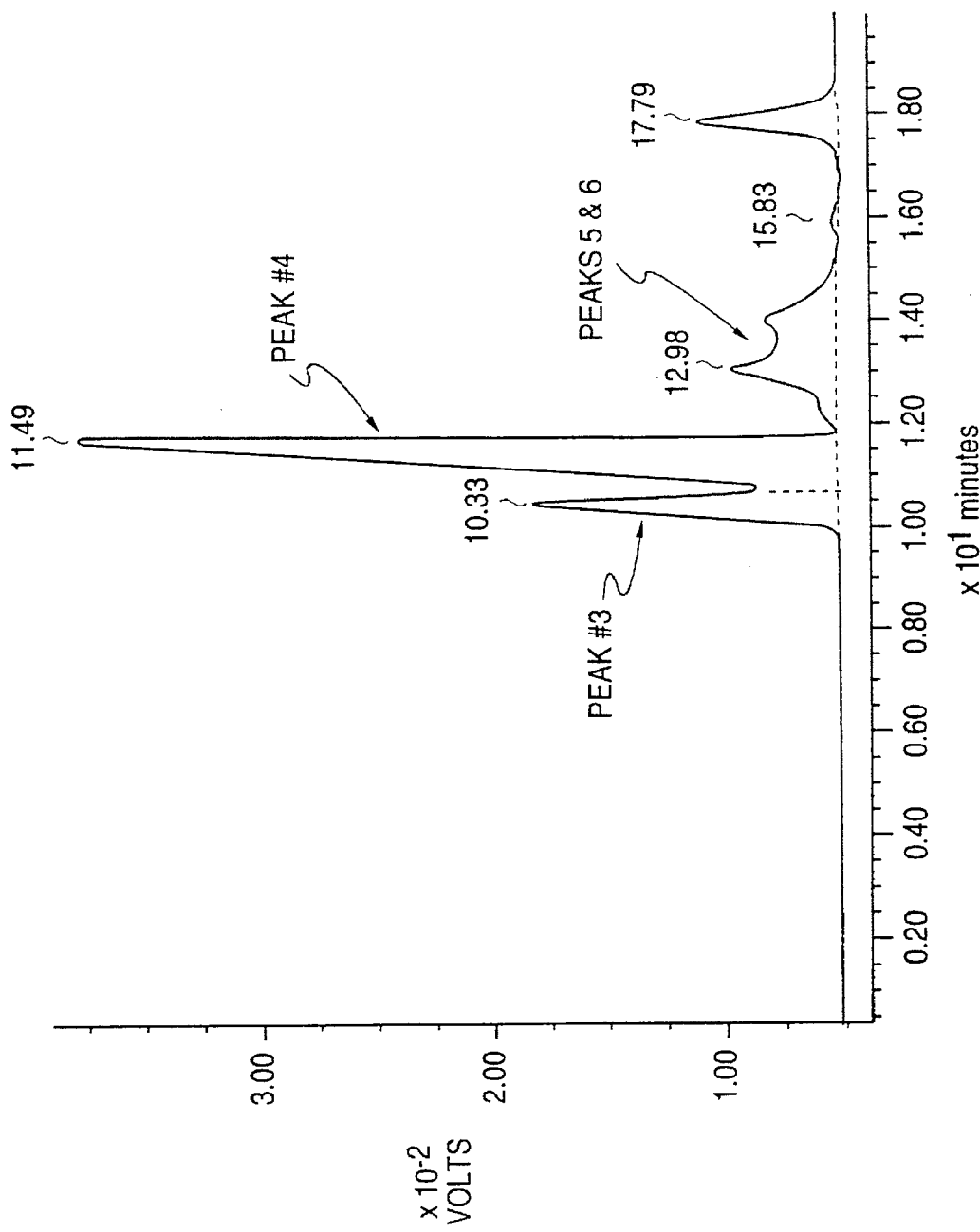
FIGS. 1–3, respectively, are high performance liquid chromatography size exclusion chromatograms for the products of Examples 1–3.

While the invention will be described in connection with specific and preferred embodiments, it will be understood that it is not intended to limit the invention to those embodiments. On the contrary, it is intended to cover all alterations, modifications and equivalents as may be included within the spirit and scope of the invention as defined by the appended claims.

Prior to the detailed description of the present invention, the analytical chromatographic, ferron complexation and $^{27}$Al NMR procedures for determining various values in connection with the present invention will be described.

The analytical chromatographic procedure is performed using pre-packaged Bondagel silica-based columns available from Waters Associates in 3.9 mm (ID) by 30 cm steel columns. A combination of Bondagel E-125 and/or Porosil GPC 60 A columns connected in series is used. The column mobile phase is 0.01M nitric acid. The mobile phase is pumped through the columns at a 0.5 ml/minute flow rate using a high performance liquid chromatography pump system (e.g., Waters model 501 or 510). A refractive index detector (e.g., Waters model 401 or 410) is used to detect sample fractions as they are eluted from the columns. The detector is linked to a printer or plotter to provide a chromatogram and to an integrator which measures the elution times or volumes of the fractions and the relative chromatographic peak areas. The Waters model 730 Data Module is an example of a printer, plotter integrator. Many computerized systems are also available. Microliter quantities of the aqueous antiperspirant solutions of interest are injected into the column system with a micro-syringe using an injector system such as the Waters model U6K.

Those skilled in the art will obtain size exclusion high performance liquid chromatograms which resemble those provided in the figures by judicious selection of column types, length of columns, flow rates, recorder/integrator type and sensitivity, detector type and sensitivity. Furthermore, those skilled in the art will be able to make peak assignments, relative to appropriate standards, so that peak 3 and peak 4 will be easily distinguishable from other peaks of shorter and longer relative retention times.

To elaborate, peak 3 and peak 4 always elute in sequential order, that is, peak 3 is prior to arid distinguishable from the subsequent peak 4 (peak 3 elutes at shorter retention times than peak 4). These peaks fall within a HPLC peak series which elute in order of decreasing apparent molecular volume. The earliest peak, designated as peak 1, representing the highest molecular volume, may not contain aluminum and may only be present in polymeric species of the antiperspirant composition and not the antiperspirant material of the present invention. Peaks 2–8 are present in both mixed metal systems (e.g., aluminum/zirconium) and in non-mixed metal systems containing only aluminum. Peak 8 is due to the totally included species (limit of column interstitial volume) most likely due to inorganic acid. Relative retention times have been calculated for each of the chromatographic peaks as the ratio of their retention times to the retention time of this totally included group of molecular species. Average values of 0.61 for peak 3 (0.59–0.64) and 0.69 for peak 4 (0.64–0.75) have been found. The exact retention times (or relative retention times) of each peak can be reproduced accurately. However, comparison to a standard basic aluminum polymer solution HPLC size exclusion chromatogram alleviates any problems caused by flow rate deviations, column bed degradation or sample preparation adjustments (concentration, injection volume, etc.)

Peak areas as reported are calculated by a chromatographic algorithm which integrates the area under each peak from its start to finish as the peak boundaries touch a horizontal baseline as a reference point. If resolution of two adjacent peaks is inadequate, a perpendicular line from the lowest point of the valley between them is dropped to the horizontal baseline to designate the endpoint of the prior peak and the starting point of the subsequent peak. These areas are then mathematically totalled and the percentage of each peak area relative to the total chromatographic peak areas is reported.

The reaction is monitored by removing aliquots of reaction medium every 0.5 hour. The heating is discontinued once the HPLC profile corresponds to the previously mentioned peak parameters. This is followed by filtering off the excess aluminum, and, if a solid or powder form is desired, by spray-drying of the solution.

The ferron complexation reaction procedure is performed by following the reaction of the ferron reagent (L) with the polyhydroxyaquoaluminum species. The absorbance at 368 nm of the aluminum ion-ferron reagent complex ($ALL_3$) was monitored over time relative to that of the free ligand (L). The liquid solution was prepared by the addition of 5 ml of a $5.7 \times 10^{-3}$ molar ferron solution, 2 milliliters; of a 1.4 molar hydroxylamine hydrochloride/0.48 molar hydrochloric acid solution, and 2 milliliters of a 2.6 molar sodium acetate solution to 25 milliliters of deionized water. The amine/weak acid salt combination buffers the solution at pH 5. To this, 2 milliliters of a 0.02% (w/w) aluminum sample (approximately $1.5 \times 10^{-3}$ molar Al) is added and the absorbance of the analyte solution is recorded within three minutes and every 30 minutes thereafter up to 6 hours. Daily readings were taken up to 10 days. The absorbance due to the $AlL_3$ complex was determined at each time period and sequential absorbance differences between absorbance values at 3 minutes, 6 hours and 10 days provided the $Al^a$ (low molecular weight), $Al^b$ (intermediate oligomeric size) and $Al^c$ (larger polymeric species) distribution in aqueous solution.

The $^{27}Al$ NMR technique and the method of calculating the $^{27}Al$ NMR resonance line areas are as follows: $^{27}Al$ NMR data were collected on either a SDS 360-1 ($v_L$= 94.676MHz) or a SDS 360-2 ($v_L$=93.788MHz) instrument. Data were collected from approximately +160 to –100 ppm, using a 90° pulse (or less, if the signal was saturating the receiver electronics) and a recycle delay of 250 ms. This optional length of the recycle delay was determined from a simple progressive saturation experiment. Sample concentrations were 10% w/w (about 400 mg/4 gm $D_2O$ solution). 10 mm quartz NMR tubes (Wilmad) were used. No H-decoupling was employed due to sample heating which caused signal modification. All spectra were corrected for background by the subtraction of a $D_2O$ blank spectrum. Tetrahedral and octahedral resonance line areas, obtained from the background-corrected spectra, were quantified by comparison to a series of reprocessed spectra. These left-shifted reprocessed spectra were obtained by sequentially removing 50, 100 and 150 μsec from the intensity vs. time FID (free induction decay) signal from each sample. This reprocessing separates broad field octahedral contributions from the less broad tetrahedral and octahedral signals in the resulting frequency vs. time spectrum after Fourier transform of the modified FID.

The relative resonance line areas (as a percentage of total resonance line areas) were obtained by dividing the integral curve height of a particular resonance line by the sum of the integral curve heights of all the resonance lines. This can be done, since the integral curve: heights are directly proportional to the resonance line areas. For example.:

$$R_A = \left[ I_A / \sum_{i=1n} I_i \right] \times 100$$

where $R_A$ is the percent of the total resonance line areas occupied by resonance line A, $I_A$ is the integral curve height of resonance line A, and $I_i$ is the integral curve height for the ith resonance line. The percent area occupied by the 71.5–73.5 resonance line, of the combined areas of the 62.5–63.5 ppm and 71.5–73.5 ppm resonance line areas, is calculated as follows:

$$R_B = [I_B/(I_C + I_B)] \times 100$$

where $R_B$ is the percentage of the combined areas of the 62.5–63.5 ppm and the 71.5–73.5 ppm resonance lines occupied by the 71.5–73.5 ppm resonance line area, $I_B$ is the integral curve height of the 71.5–73.5 ppm resonance line and $I_C$ is the integral curve height of the 62.5–63.5 ppm resonance line.

The present invention contemplates basic aluminum materials (that is, polymeric basic aluminum compounds) having the empirical formula:

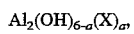

$$Al_2(OH)_{6-a}(X)_a,$$

where $0.5 \leq a \leq 5$ and where X is a univalent complex oxoanion of nitrogen or halogen having specified characteristics, characterized by:

(a) a peak 4 relative area of at least 25%, and a peak 3 relative area of less than 60%, the sum of the relative peak 3 and peak 4 areas being at least 50%;

(b) less than 10% chromatographic peaks eluting at shorter retention times than peak 3, corresponding to peaks 1 and 2; (c) less than 25% of the aluminum in the form of $Al^b$ polyhydroxyaquoaluminum;

(d) an $^{27}Al$ NMR spectrum wherein 5%–30%, preferably 8%–18%, of the total area under the spectrum from 140 ppm to –80 ppm is contained in a resonance line at 71.5–73.5 ppm; and (e) an $^{27}Al$ NMR spectrum in which the area of the 71.5–73.5 ppm resonance line includes more than 50% of the combined areas of the 62.5–63.5 ppm and 71.5–73.5 ppm resonance lines.

Moreover, the present invention contemplates methods of forming such basic aluminum materials, by reacting aluminum metal with an aluminum salt to form the basic aluminum materials (which aluminum salt can be prepared in situ from aluminum metal and an inorganic acid.), wherein the aluminum metal added is provided so as to achieve a low aluminum metal surface area in order to achieve the amount of aluminum in the form of $Al^b$ polyhydroxyaquoaluminum, and the $^{27}Al$ NMR spectrum, as set forth in the previous paragraph.

In addition, the present invention contemplates antiperspirant compositions including such above-described basic aluminum material, another antiperspirant active material (e.g., a metal salt active antiperspirant material) and optionally a neutral amino acid, and methods of forming such compositions.

The present invention further contemplates forming basic aluminum materials by reacting aluminum with the aluminum salt, in solution, with the aluminum being added in stoichiometric or near-stoichiometric amounts (rather than adding the aluminum metal in large excess), so as to achieve the basic aluminum material having:

(1) for the $^{27}$Al NMR spectrum,
  (a) a 71.5–73.5 ppm resonance line including at least 5% of the total area of the NMR spectrum, and up to and including 30% of the total area, preferably 8%–18% of the total area,
  (b) a 0–5 ppm resonance line including at least 5% of the total NMR area, and up to and including 30% of the total area, and
  (c) a 62.5–63.5 ppm resonance line including less than 10% of the total area of the NMR spectrum;

(2) a size exclusion HPLC chromatogram which contains:
  (a) a peak 4 relative area of at least 40%, a peak 3 relative area of less than 30%, the sum of the relative peak 3 and peak 4 areas being at least 50%,
  (b) a combined peak 5 and peak 6 relative area of at least 15%, and
  (c) less than 10% chromatographic peaks eluting at shorter retention times than peak 3, corresponding to peaks 1 and 2; and (3) less than 25% of the total aluminum in the form of $Al^b$ polyhydroxyaquoaluminum.

As discussed previously, in one aspect of the invention described in U.S. patent application Ser. No. 07/233,008, filed Aug. 17, 1988, and in its continuation-in-part application filed May 2, 1990, a basic aluminum material is disclosed wherein at least 25% by weight of the basic aluminum material is in the form of $Al^b$ polyhydroxyaquoaluminum. It has since been learned that this embodiment contains at least 5%, and usually less than 50%, of the total aluminum in the form of polymers having a characteristic resonance line in the $^{27}$Al NMR spectrum. This line is 62.5–63.5 ppm downfield from the resonance line of $Al^{3+}$ (6H$_2$O). This line has been attributed to the presence of a complex ion $[Al_{13}O_4(OH)_{24}(H_2O)_{12}]^{7+}$ by Akitt, et al, in *J.C.S. Dalton Transactions* (1972), page 604. This complex ion is also known as an $Al_{13}$-mer. This $Al_{13}$-mer is associated with $Al^b$ polyhydroxyaquoaluminum in the article by Fitzgerald, "Chemistry of Basic Commercial Aluminum Hydrolysis Complexes" in Laden, et al, *Antiperspirants And Deodorants* (1988), pages 225–227.

Furthermore, it has also been learned that the embodiment containing at least 25% by weight of the basic aluminum material in the form of $Al^b$ polyhydroxyaquoaluminum, in U.S. patent application Ser. No. 07/233,008, exhibits a characteristic resonance line in the $^{27}$Al NMR spectrum which is 71.5–73.5 ppm downfield from the resonance line of $Al^{3+}$(6H$_2$O). The area of the 71.5–73.5 ppm resonance line of the aforementioned basic aluminum material of No. 07/233,008 comprises between 0% and 50% of the combined area of the 62.5–63.5 ppm and 71.5–73.5 ppm resonance line areas. Surprisingly, however, an even further enhanced antiperspirant activity is achieved by a basic aluminum material containing significantly less aluminum in the form of $Al^b$ polyhydroxyaquoaluminum, and significantly less aluminum in the form of polymers characterized by an $^{27}$Al NMR resonance line at 62.5–63.5 ppm and significantly more aluminum in the form of polymers characterized by a $^{27}$Al NMR resonance line at 71.5–73.5 ppm.

As indicated previously, according to the present invention the aluminum added to the aluminum salt in solution, to form the basic aluminum materials, has a low aluminum metal surface area. While not limiting, such low aluminum metal surface area can be achieved in at least two ways, as follows:

(1) Aluminum metal of any shape or size, excluding ingots and including powder, but preferably between 0.005 inch and 0.1 inch (0.13 mm–2.5 mm) in diameter if spherical or 0.03 inch-0.25 inch (0.75 mm–6.4 mm) long oblong and 0.005 inch-0.05 inch (0.13 mm—1.3 mm) thick if not spherical ( for example, small turnings), can be added to the vessel containing a solution of $Al(Y'''O_n)_3$ at a molar ratio of aluminum metal to $Al(Y'''O_n)_3$ which is between 0.5 and 2.5, to form the desired basic aluminum material $Al_2(OH)_{6-a}$ $(Y^zO_n)_a$, where a, z and n are as previously defined. This aluminum to $Al(Y'''O_n)_3$ molar ratio of 0.5–2.5 is considerably lower than the molar ratio of aluminum metal to aluminum halide used in the preparation of conventional basic aluminum halides.

and/or

2. Aluminum metal can be added to the $Al(Y'''O_n)_3$ solution in excess of the aforementioned molar ratio of 2.5, provided that the aluminum metal is of sufficiently large particle size. In this aspect of the present invention, it is preferable not to use aluminum powder or small turnings as described previously (that is, small turnings 1/16 inch to 1/8 inch long oblong pieces and 1/100 inch to 3/100 inch thick). Aluminum turnings, spheres, prills, shot, etc., nominally greater than 0.1 inch (2.5 mm) in thickness, preferably between 0.1 inch and 0.4 inch (2.5 mm–10 mm) are examples of sufficiently large particle size for the aluminum metal.

Apart from the amount and/or size of the particles of aluminum utilized in forming the basic aluminum material according to the present invention, the processing techniques are the same as described in U.S. patent application Ser. No. 07/233,008, filed Aug. 17, 1988 and the continuation-in-part application thereof filed May 2, 1990. In addition, apart from the basic aluminum material, the antiperspirant compositions, and methods of making such compositions, correspond to the compositions and methods for forming the compositions as set forth in U.S. patent application Ser. No. 07/233,008, filed Aug. 17, 1988, and its continuation-in-part application filed May 2, 1990. The contents of each of the U.S. patent applications Ser. No. 07/233,008, filed Aug. 17, 1988, and the continuation-in-part application thereof filed May 2, 1990, have been incorporated herein in their entirety by reference.

The materials and compositions of the present invention can be incorporated as a substitute for the active antiperspirant substance in various conventional antiperspirant forms for axillary application, such as aqueous and alcoholic solutions, solid sticks, roll-ons (suspensions of dried active material, lotions, solutions, water-in-oil emulsions or oil-in-water emulsions), gels, creams, compressed powders, aerosols, etc. Attention is directed to U.S. Pat. No. 4,359,456, U.S. Pat. No. 4,606,915 and British patent specification No. 1,568,831, for their disclosures of various components, utilized in antiperspirant compositions, with which the material and composition of the present invention can be blended for forming antiperspirants for axillary application. The materials and compositions of the present invention are used in antiperspirants in amounts equal to and greater than the amounts of conventional enhanced activity antiperspirant materials used in antiperspirants. For example, any emulsion (water-in-oil or oil-in-water) antiperspirant roll-on product can be prepared with 10–25% by weight of the materials and/or compositions of the present invention without concern for the loss of enhanced antiperspirant activity.

Various specific examples of the present invention are set forth in the following. Of course, such examples are illustrative and not limiting. In connection with the following examples are provided size exclusion chromatograms, and $^{27}$Al NMR diagrams, for products formed in such examples. Such chromatograms, and such $^{27}$Al NMR diagrams, were obtained utilizing the analytical procedures discussed previously. The ferron results are on a weight % basis of the basic aluminum material.

EXAMPLE 1

Figure 4:
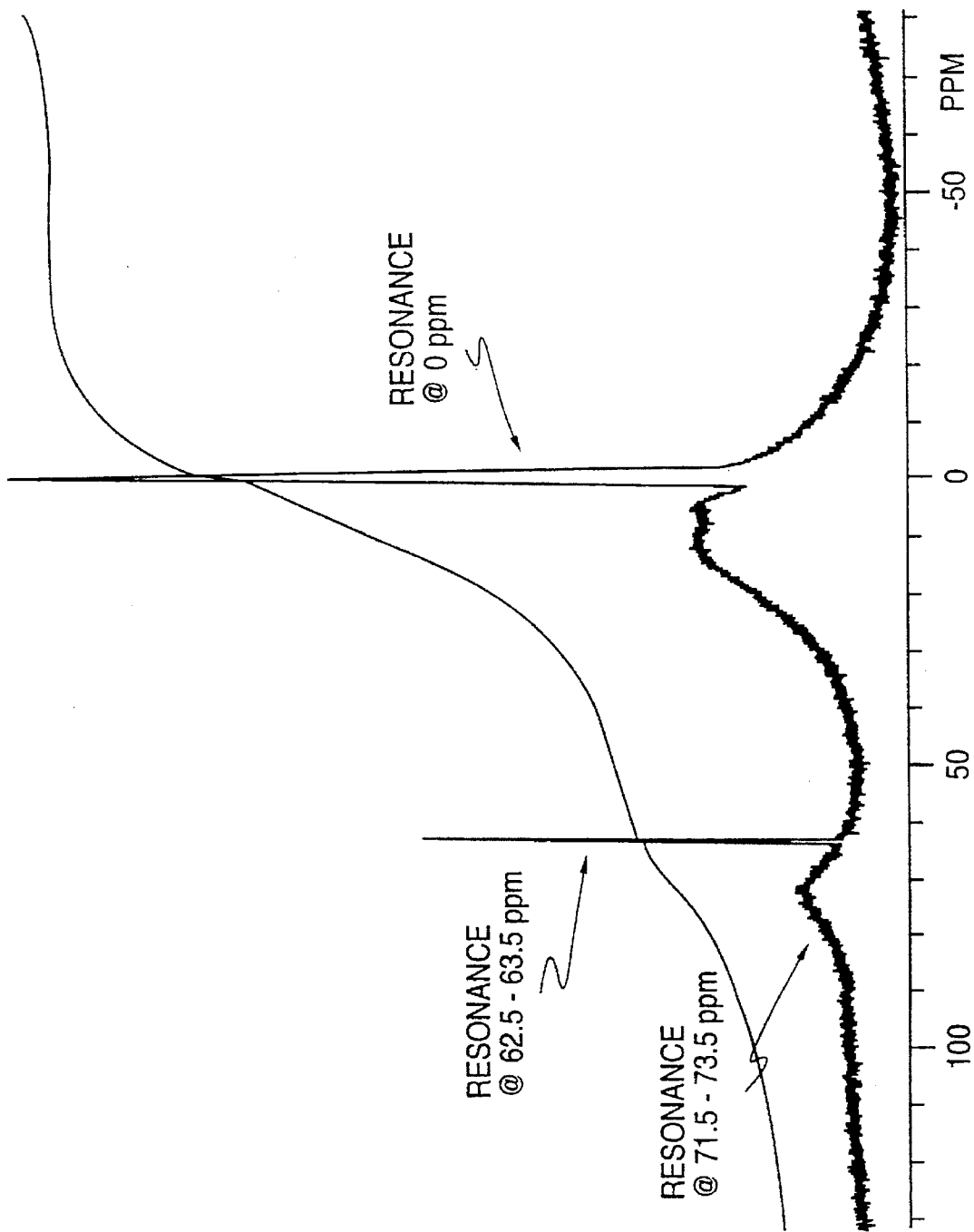
FIGS. 4–6 are $^{27}$Al nuclear magnetic resonance (NMR) diagrams for the products of Examples 1–3, respectively.

46.6 grams of aluminum nitrate nonahydrate are dissolved in deionized water to give 248.6 grams of total solution. The resultant 0.50M solution is heated to 95° C. over a thirty minute period. 6.0 grams of aluminum metal in the form of small turnings, approximately 1/16" to 1/8" long oblong pieces, 1/100" to 3/100" thick, are added over a two minute period. Thus, a low molar ratio of aluminum metal to aluminum nitrate is used. A reaction temperature of 95°–99° C. is maintained with continuous stirring. After a total of 6 hours from the addition of aluminum metal, the reaction mixture is quickly filtered hot to remove unreacted aluminum, if any. The solution is rapidly spray dried. Analytical analysis of the spray-dried powder indicates that it contains 21.76% aluminum and 7.19% nitrogen. A 15% solution of this spray-dried powder in deionized water is found to exhibit a pH of 3.84. A 10% solution contains 16.4% peak 3 area, 56.4% peak 4 area, a combined 18.1% peak 5 and peak 6 areas and no earlier chromatographic peaks, as shown in FIG. 1. The ferron reaction results in 10.4% $Al^a$, 20.1% $Al^b$ and 69.5% $Al^c$. The $^{27}$Al NMR of a 10% aqueous solution of the spray-dried powder is shown in FIG. 4. As can be seen, the 71.5–73.5 ppm resonance line area is 11% of the total NMR resonance line area, the 62.5–63.5 ppm resonance line area is 1% of the total resonance line area, the 71.5–73.5 ppm resonance line area comprises 93% of the combined 62.5–63.5 ppm and 71.5–73.5 ppm line areas, and the 0–5 ppm resonance line area is 7.2% of the total resonance line area.

EXAMPLE 2

Figure 2:
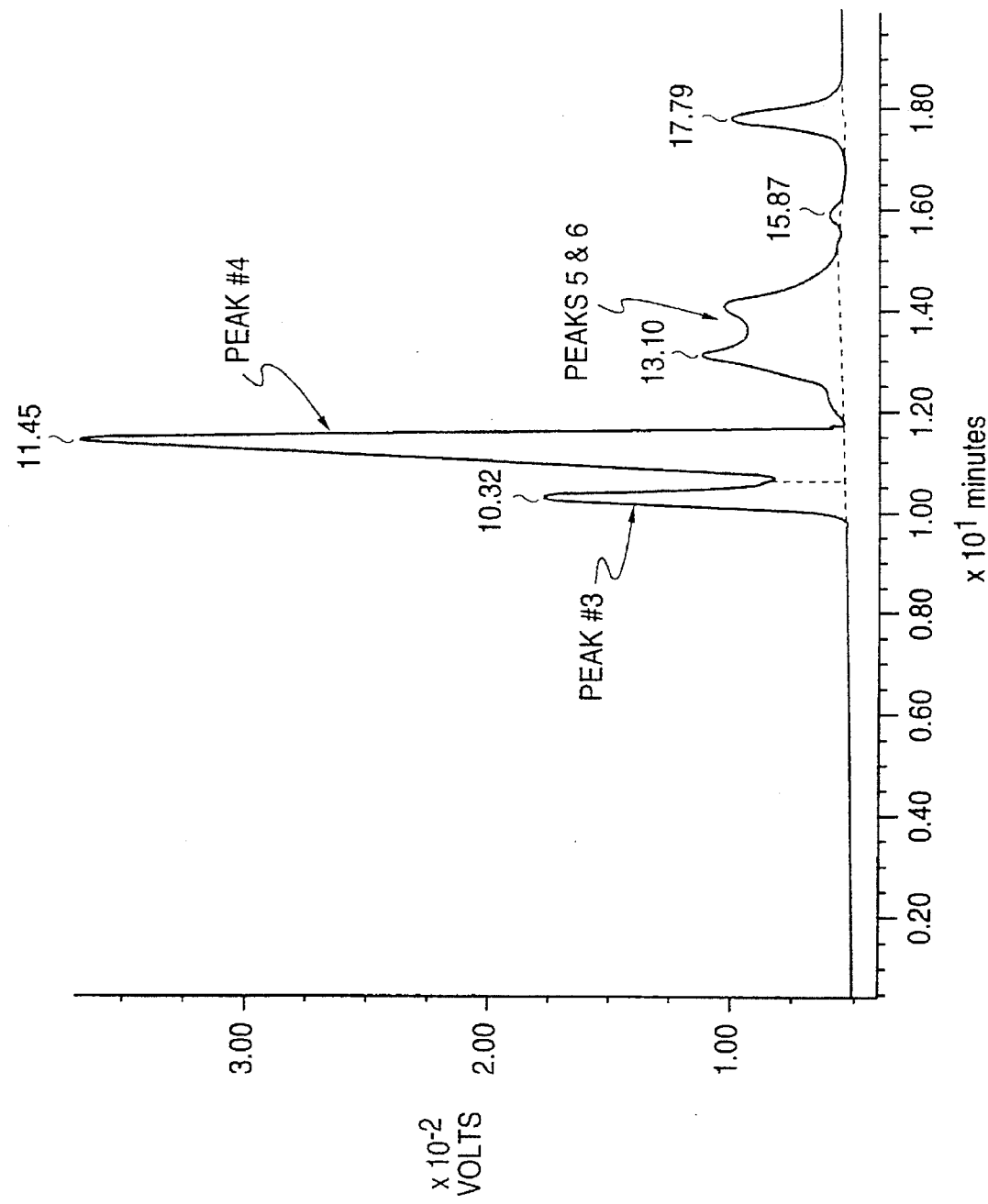
Figure 5:
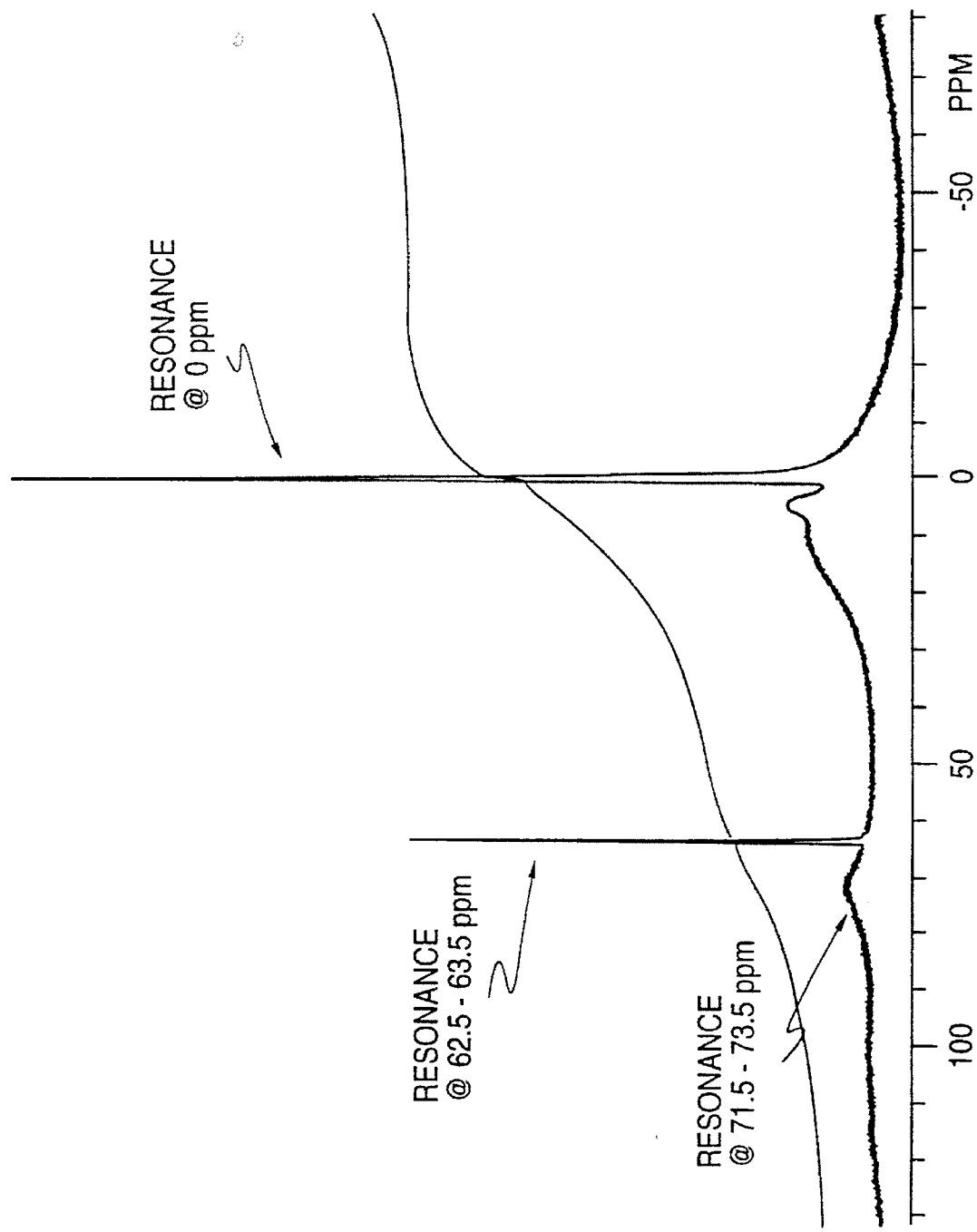

46.6 grams of aluminum nitrate nonahydrate are dissolved in deionized water to give 248.6 grams of total solution. The resultant 0.50M solution is heated to 95° C. over a thirty minute period. 6.0 grams of aluminum metal in the form of small turnings, approximately 1/16" to 1/8" long oblong pieces, 1/100" to 3/100" thick, are added over a two minute period. Thus, a low molar ratio of aluminum metal to aluminum nitrate is used. A reaction temperature of 95°–99° C. is maintained with continuous stirring. After a total of 5 hours from the addition of aluminum metal, the reaction mixture is quickly filtered hot to remove unreacted aluminum, if any. The solution is rapidly spray-dried. Analytical analysis of the spray-dried powder indicates that it contains 20.52% aluminum and 7.87% nitrogen. A 15% solution of this spray-dried powder in deionized water is found to exhibit a pH of 3.81. A 10% solution contains 14.9% peak 3 area, 50.7% peak 4 area, a combined 26.6% peak 5 and peak 6 areas and no earlier chromatographic peaks, as shown in FIG. 2. The ferron reaction results in 14.8% $Al^a$, 22.0% $Al^b$ and 63.2% $Al^c$. The $^{27}$Al NMR of a 10% aqueous solution of the spray-dried powder is shown in FIG. 5. As can be seen, the 71.5–73.5 ppm resonance line area is 11% of the total NMR resonance line area, the 62.5–63.5 ppm resonance line area is 1.4% of the total resonance line area, the 71.5–73.5 ppm resonance line area comprises 88% of the combined 62.5–63.5 ppm and 71.5–73.5 ppm line areas, and the 0–5 ppm resonance line area is 9.6% of the total NMR resonance line area.

EXAMPLE 3

Figure 3:
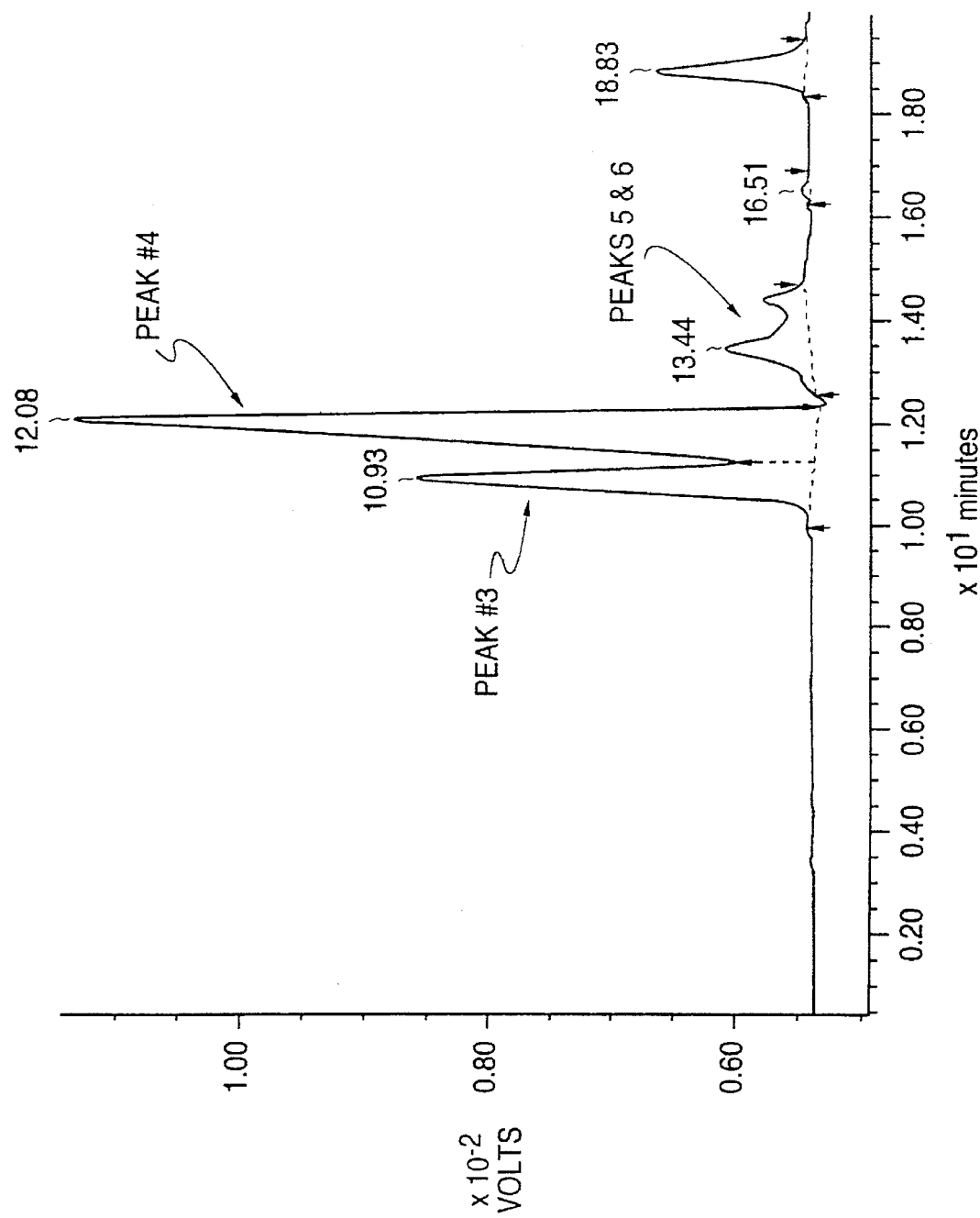
Figure 6:
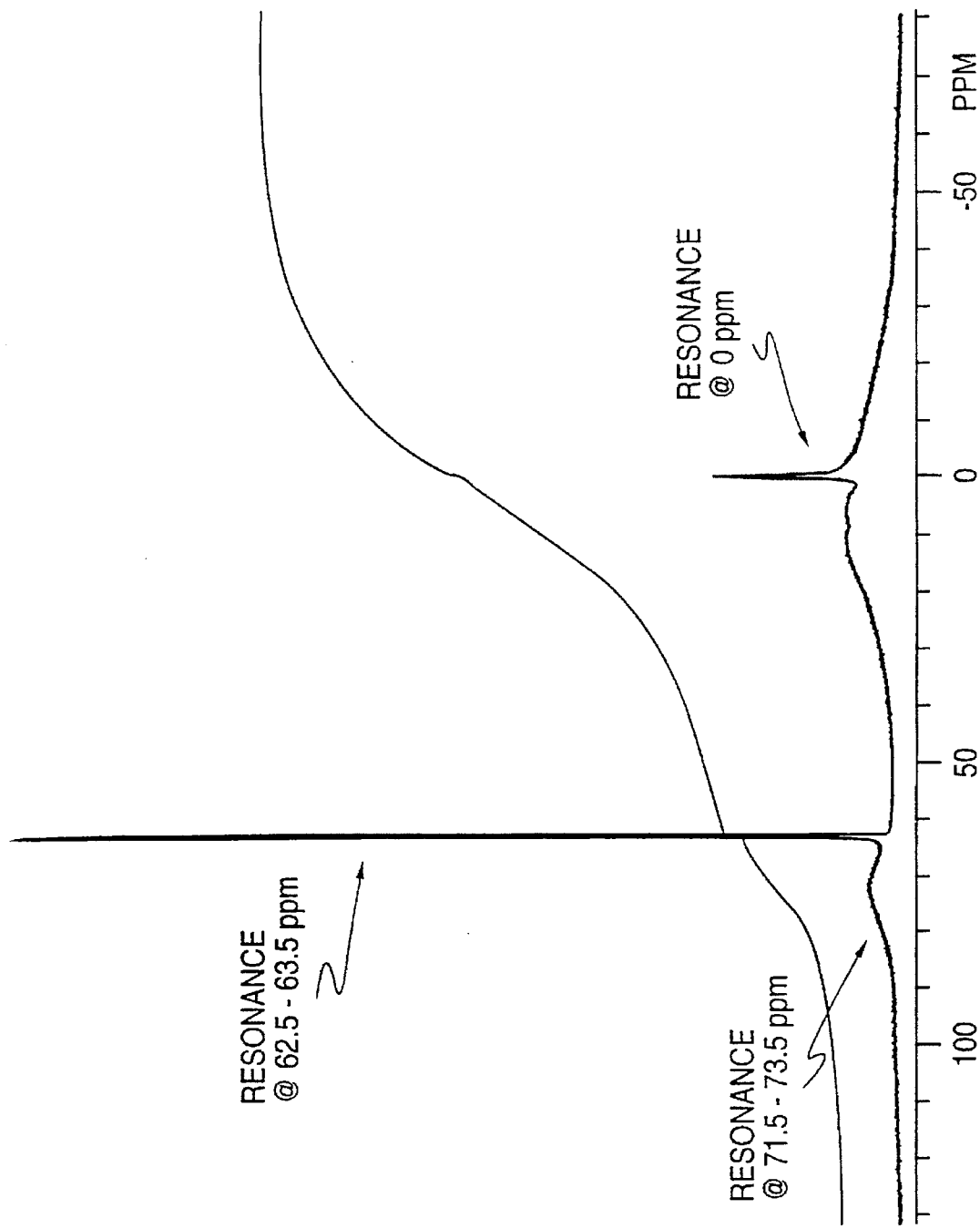

28.1 grams of aluminum nitrate nonahydrate are dissolved in deionized water to give 100.0 grams of total solution. The resultant 0.75M solution is heated to 95° C. over a thirty minute period. 16.2 grams of aluminum metal in the form of spherical-like shot, approximately 0.03" to 0.175" (0.76 mm–4.4 mm) in diameter, are added over a two minute period. This example uses an excess of aluminum metal, having a large shot size. A reaction temperature of 95°–99° C. is maintained with continuous stirring. After a total of 3.5 hours from the addition of aluminum metal, the reaction mixture is quickly filtered hot to remove unreacted aluminum, if any. The solution is rapidly spray-dried. Analytical analysis of the spray-dried powder indicates that it contains 22.16% aluminum and 6.73% nitrogen. A 15% solution of this spray-dried powder in deionized water is found to exhibit a pH of 4.10. A 10% solution contains 24.4% peak 3 area, 59.9% peak 4 area, a combined 8.1% peak 5 and peak 6 areas and no earlier chromatographic peaks, as shown in FIG. 3. The ferron reaction results in 6.1% $Al^a$, 24.9% $Al^b$ and 70.0% $Al^c$. The $^{27}$Al NMR of a 10% aqueous solution of the spray-dried powder is shown in FIG. 6. As can be seen, the 71.5–73.5 ppm resonance line area is 12.4% of the total NMR resonance line area, the 62.5–63.5 ppm resonance line area is 3.1% of the total resonance line area, the 71.5–73.5 ppm resonance line area comprises 80% of the combined 62.5–63.5 ppm and 71.5–73.5 ppm line areas, and the 0–5 ppm resonance line area is 3.6% of the total NMR resonance line area.

EXAMPLE 4

Figure 7:
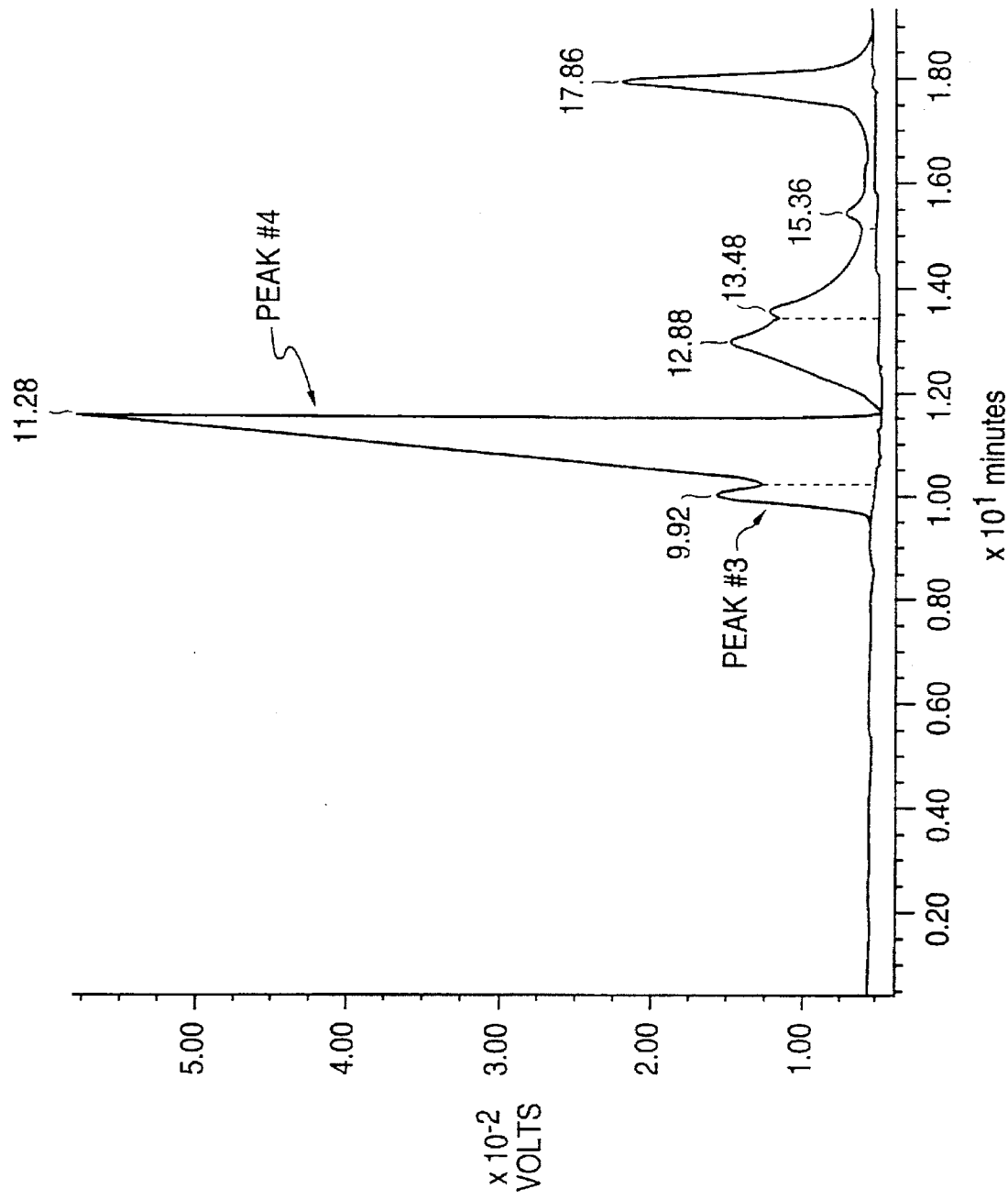
FIGS. 7–9 are high performance liquid chromatography size exclusion chromatograms for the product of Example 4, at specified times after addition of aluminum metal to the solution of the aluminum salt.
Figure 8:
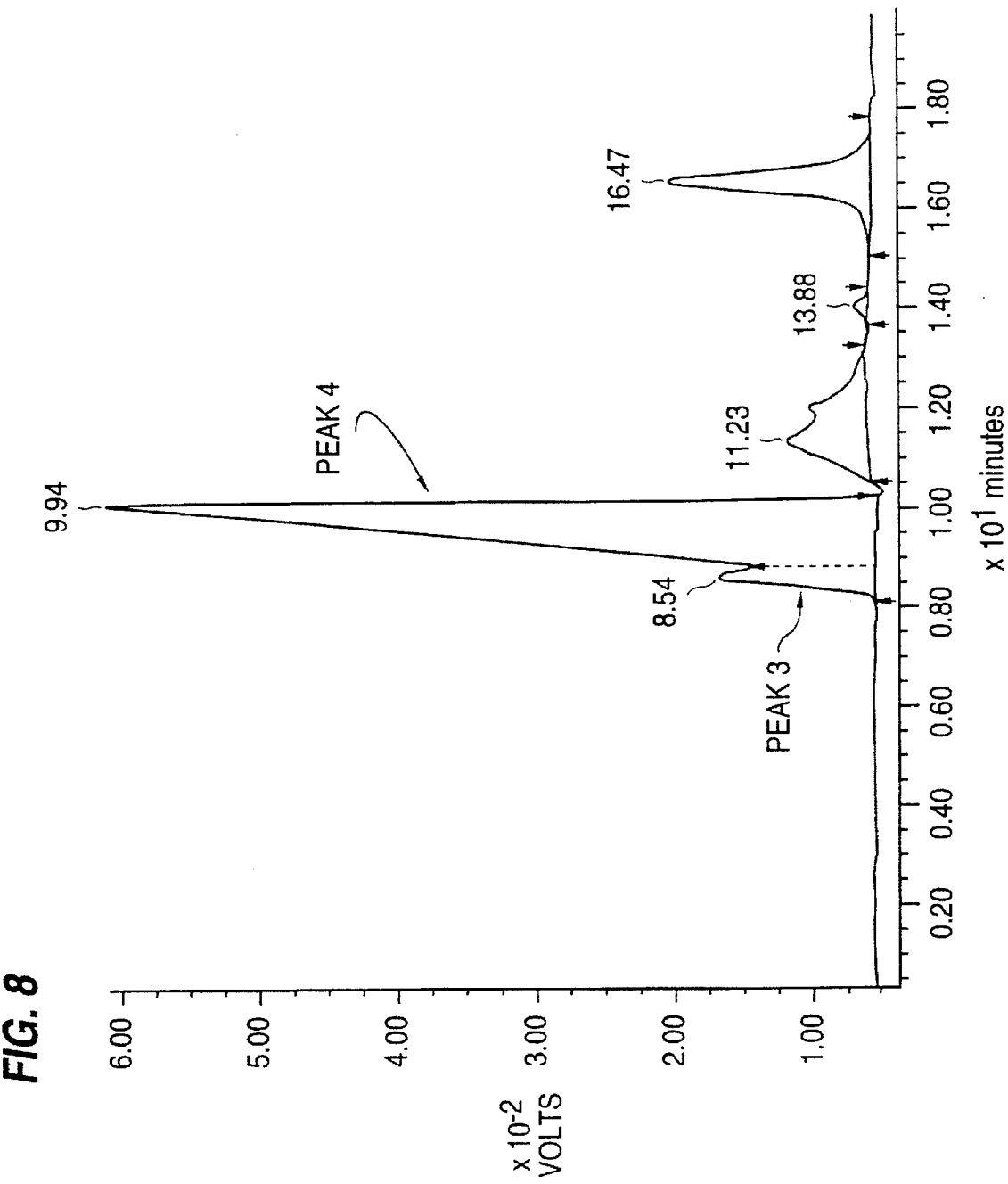
Figure 9:
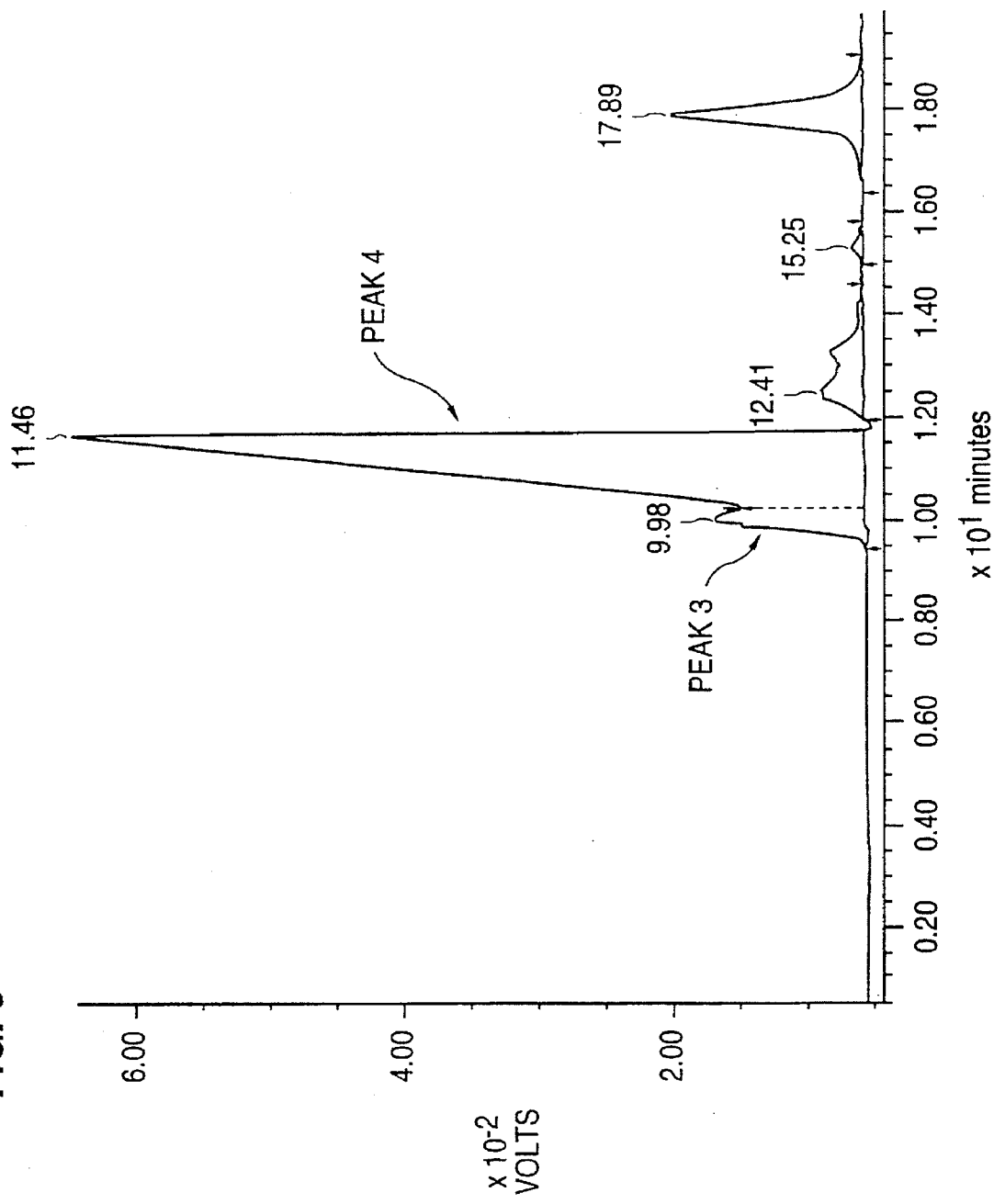

69.9 grams of aluminum nitrate nonahydrate are dissolved in deionized water to give 248.4 grams of total solution. The resultant 0.75M solution is heated to 85°–90° over a thirty minute period. 9.03 grams of aluminum metal (the stoichiometric amount required), as small turnings, are added over two minutes. Thus, a low molar ratio of aluminum metal to aluminum nitrate is used. The reaction temperature is raised to 95°–100° C. and maintained at this temperature for at least 3 hours, or until all of the aluminum metal has dissolved. Peak 3 area remains below 10% of the total peak area even 7 hours post-aluminum metal addition. After 4 hours post-aluminum metal addition, the resultant solution exhibits 5.86% peak 3 area, 56.94% peak 4 area and no earlier chromatographic peaks, as shown in FIG. 7. After 5 hours post-aluminum metal addition and at 95°–100° C., the solution exhibits 7.35% peak 3 area, 68.87% peak 4 area and no earlier peaks, as shown in FIG. 8. After 6.5 hours, the same solution exhibits 6.81% peak 3 area, 76.35% peak 4 area and no earlier chromatographic peaks as shown in FIG. 9. Thus, a long reaction time is used. Isolation of solid can be accomplished by spray- or freeze-drying.

COMPARATIVE EXAMPLE 1

Figure 10:
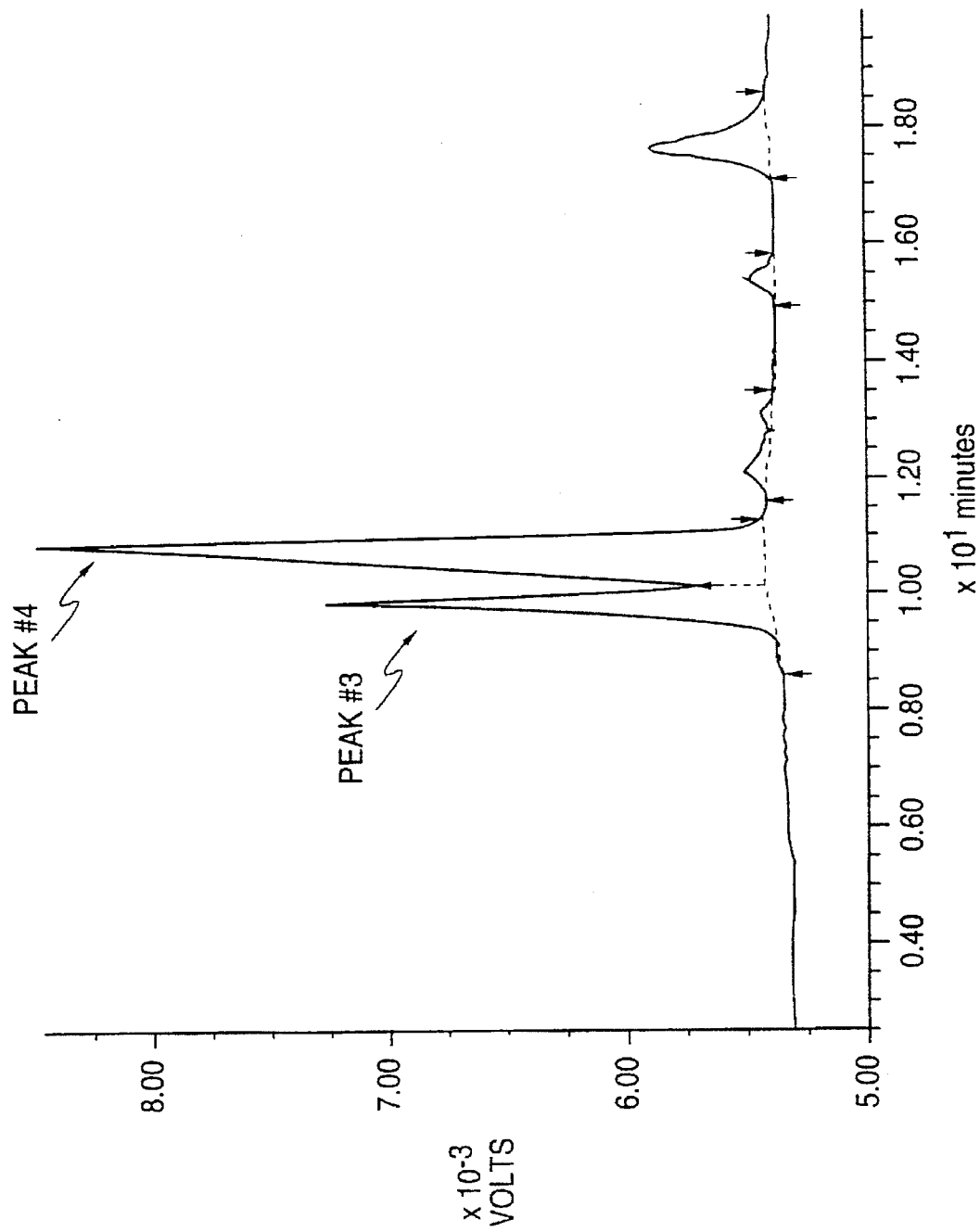
FIG. 10 is a high performance liquid chromatography size exclusion chromatogram for the product of Comparative Example 1.
Figure 11:
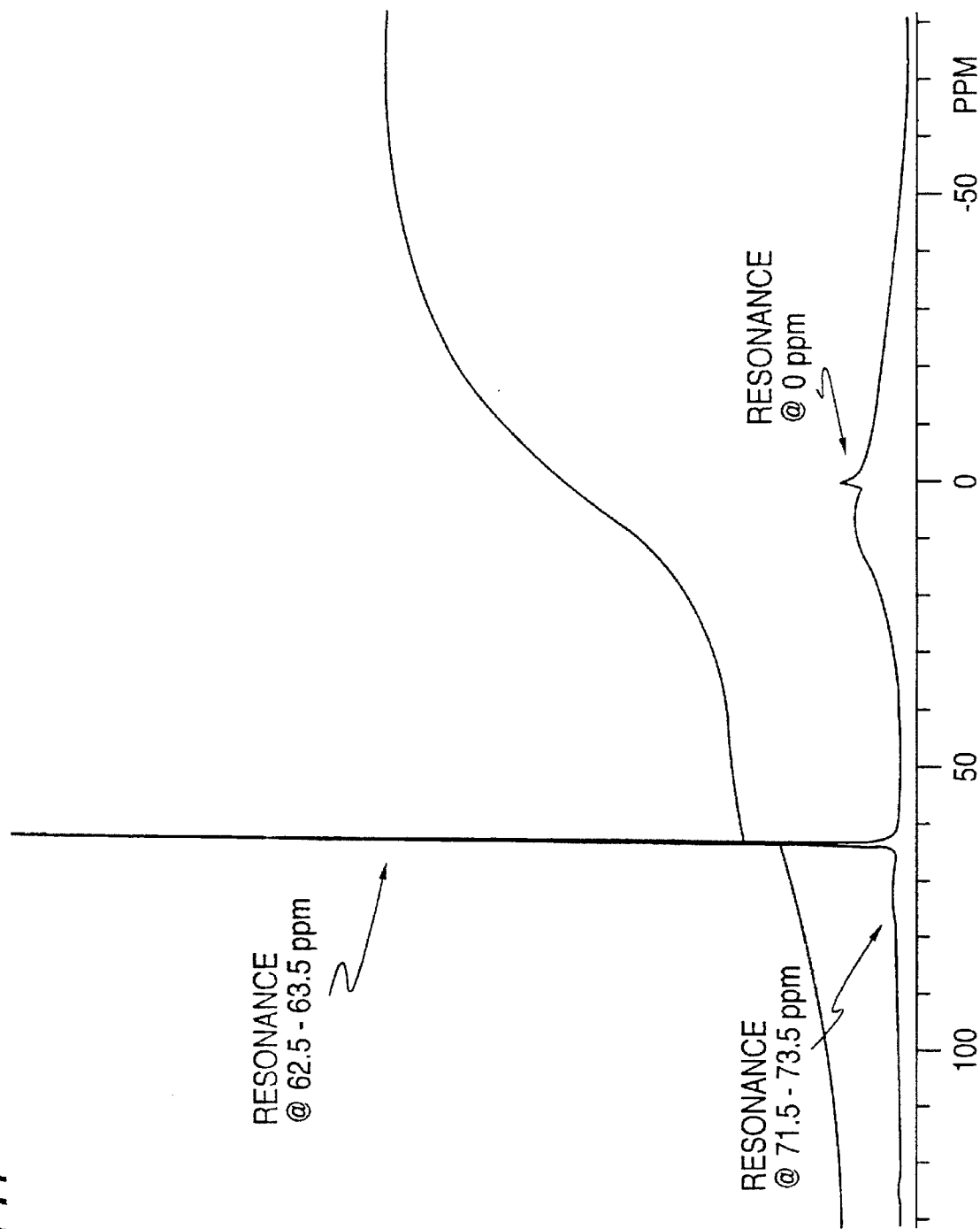
FIG. 11 is a $^{27}$Al NMR diagram for the product of Comparative Example 1.

Aluminum nitratohydrate was prepared according to a technique described in application Ser. No. 07/233,008, filed Aug. 17, 1988. 349.5 grams of aluminum nitrate nonahydrate are dissolved in 892.5 grams of deionized water. The resultant 0.75M solution is heated to 65°–70° C. with continuous stirring, and 250.9 grams of aluminum metal (small turnings, approximately 1/16" to 1/8" long oblong pieces, 1/100" to 1/300" thick), are added in excess over a five minute period. A reaction temperature of 70°–95° C. is maintained with continuous stirring. After a total of 3.7 hours from the addition of aluminum metal, the reaction mixture is filtered hot to remove the unreacted aluminum metal. The resultant solution contains 58.5% HPLC peak 4 relative area, 24.1% relative peak 3 area, and no earlier chromatographic peaks. The solution is then spray-dried. A 10% aqueous solution of the spray-dried powder contains 57.4% peak 4 relative area, 27.8% peak 3 relative area and no earlier chromatographic peaks, as shown in FIG. 10. The ferron reaction results in 14.9% $Al^a$, 44.1% $Al^b$, and 41.0% $Al^c$. The $^{27}Al$ NMR of a 10% aqueous solution of the spray-dried powder is shown in FIG. 11. As can be seen, the 71.5–73.5 ppm resonance line area is barely perceptible at less than 1% of the total NMR resonance line area, the 62.5–63.5 ppm NMR resonance line area is 8% of the total resonance line area, and the 0–5 ppm resonance line area comprises 2% of the total NMR resonance line area.

The basic aluminum material from Example 3 and from Comparative Example 1 were separately evaluated in two separate antiperspirant clinical studies at an independent testing laboratory. The two above-mentioned basic aluminum materials were tested as spray-dried powders suspended in a non-aqueous base containing volatile silicone and stearyl alcohol. The concentration of the spray-dried powders in the base was 24%–25% by weight.

The clinical protocol for each study was identical. Approximately 45 adult female subjects age 18 through 65 completed the studies. Each subject abstained from the use of all antiperspirants 17 days prior to treatment with the test materials. Test treatment was distributed as treatment pairs for application during the test period so that two different treatments, on contralateral axillae, were randomized for right and left axillary assignments among the total number of subjects. Sweating of the subjects was induced by having the subjects sit in a "hot room" maintained at 100°±2° F. and at a relatively humidity of about 35%. During the first 40 minutes of sweat stimulation, the subjects held unweighed Webril pads (nonwoven cotton padding fabric) in their axillae. This preliminary warm-up period was followed by two successive 20 minute collection periods, during which the subjects held preweighed Webril pads in their axillae. These Webril pads were weighed before and after each 20 minute collection. The amount of sweat collected in each 20 minute period was used as an independent measurement of sweat output. Sweat output was obtained both prior to treatment with the test materials (to establish a pre-treatment base line sweat output value) and 24 hours following the fourth treatment. Test material treatment consisted of 4 daily doses of 0.5 grams of the above-mentioned formulation bases.

The data was analyzed using a general linear model in which the logarithm of post-treatment sweat output was a dependent variable. The logarithm of base line sweat output was a covariate. A modification of the Wooding and Finkelstein crossover model was used. As can be seen from the data presented in Table 1, the basic aluminum material of the present invention is a significantly more effective antiperspirant than that in Comparative Example 1.

TABLE 1

| Formulation Base Containing: | Pre-treatment Sweat Output (mg) | Post-treatment Sweat Output (mg) | % Sweat Reduction |
| --- | --- | --- | --- |
| Example 3 | 1124 | 516 | 54.1 |
| Comparative Example 1 | 1135 | 704 | 38.0 |

A similar result was obtained when the basic aluminum material from Example 2 and from Comparative Example 1 were evaluated in two separate antiperspirant clinical studies at the same independent testing laboratory.

Accordingly, by the present invention an even further enhanced activity antiperspirant material is provided, which can be produced without the necessity of using large aluminum metal surface areas or using excess aluminum (thereby decreasing costs for producing the material) and also without the necessity of using powdered aluminum (and any possible explosion hazard due to use of such powder). Moreover, according to the present invention a composition including such basic aluminum material and method of providing such composition, can easily be achieved.

While we have shown and described several embodiments in accordance with the present invention, it is understood that the same is not limited thereto, but is susceptible of numerous changes and modifications as known to those skilled in the art. Therefore, we do not wish to be limited to the details shown and described herein, but intend to cover all such changes and modifications as are encompassed by the scope of the appended claims.

We claim:

1. Antiperspirant compositions having the formula:

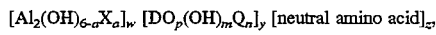

where $0.5 \leq a \leq 5.0$, X is a univalent complex oxoanion of nitrogen or a halogen, which forms salts with $Al^{3+}$ in aqueous dissociated, which is readily soluble in water with metallic ions in the solution, and which forms conjugate acids that are strong acids, w: y ranges from about 0.3:1 to about 6.0:1, z:y ranges from 0 to 1.3:1, p is either 0 or 1, where when p is O m is O and n is 4, and when p is 1 then m+n is 2, D is a metal cation selected from the group consisting of Zr, Hf, Ti and Sn, and Q is a halide or X, $Al_2(OH)_{6-a}X_a$ further being characterized by:

(a) size exclusion high performance liquid chromatography peaks corresponding to peak 3 and peak 4 of the size exclusion chromatogram produced from a high performance liquid chromatography technique;

(b) a peak 4 relative area of at least 25%, and a peak 3 relative area of less than 60%, the sum of the relative peak 3 and peak 4 areas being at least 50%;

(c) less than 10% chromatographic peaks eluting at shorter retention times that peak 3, corresponding to peaks 1 and 2;

(d) less than 25% of the aluminum being in the form of $Al^b$ polyhydroxyaquoaluminum;

(e) an $^{27}Al$ NMR spectrum wherein 5%–30% of the total area under the spectrum from 140 ppm to −80 ppm is contained in a resonance line at 71.5–73.5 ppm; and (f) an $^{27}Al$ NMR spectrum in which the area of the 71.5–73.5 ppm resonance line includes more than 50% of the combined areas of the 62.5–63.5 ppm and 71.5–73.5 ppm resonance lines.

2. Antiperspirant compositions according to claim 1, wherein z:y is greater than O.

3. Antiperspirant compositions according to claim 1, wherein the composition has a peak 4 area that is at least 25%, a peak 3 area that is less than 50%, and the sum of the peak 3 and peak 4 areas of the composition is at least 40%.

4. Antiperspirant compositions according to claim 1, wherein 8%–18% of the total area under the $^{27}Al$ spectrum from 140 ppm to −80 ppm is contained in a resonance line at 71.5–73.5 ppm.

5. An antiperspirant active composition, comprising:

(1) at least one basic aluminum material having the empirical formula:

$Al_2(OH)_{6-a}X_a$, where $0.5 \leq a \leq 5.0$; and X is a univalent complex oxoanion of nitrogen or a univalent complex oxoanion of a halogen, which form salts with $Al^{3+}$ in aqueous solution, so that these salts are essentially completely dissociated, which is readily soluble in water with metallic ions in the solution, and which forms conjugate acids that are strong acids, the at least one basic aluminum material being further characterized by:

(a) size exclusion high performance liquid chromatography peaks corresponding to peak 3 and peak 4 of the size exclusion chromatogram produced from a high performance liquid chromatography technique;

(b) a peak 4 relative area of at least 25%, and a peak 3 relative area of less than 60%, the sum of the relative peak 3 and peak 4 areas being at least 50%;

(c) less than 10% chromatographic peaks eluting at shorter retention times than peak 3, corresponding to peaks 1 and 2;

(d) less than 25% of the aluminum being in the form of $Al^b$ polyhydroxyaquoaluminum;

(e) an $^{27}Al$ NMR spectrum wherein 5% to 30% of the total area under the spectrum from 140 ppm to −80 ppm is contained in a resonance line at 71.5–73.5 ppm; and (f) an $^{27}Al$ NMR spectrum in which the area of the 71.5–73.5 ppm resonance line includes more than 50% of the combined areas of the 62.5–63.5 ppm and 71.5–73.5 ppm resonance lines, (2) at least one other antiperspirant active material, which is selected from the group consisting of antiperspirant active Zr salts, antiperspirant active Hf salts, antiperspirant active Ti salts and antiperspirant active Sn salts, and (3) a neutral amino acid.

6. An antiperspirant active composition according to claim 5, having the formula:

$[Al_2(OH)_{6-a}X_a]_w [DO_p(OH)_mQ_n]_y$ [neutral amino acid]$_z$, where a and X are as defined previously, w:y ranges from about 0.3:1 to about 6.0:1, z:y is greater than 0 and up to 1.3:1, p is either 0 or 1, when p is 0 m is 0 and n is 4, and when p is 1 then m+n is 2, D is a metal cation selected from the group consisting of Zr, Hf, Ti and Sn, and Q is a halide or X.

7. An antiperspirant composition according to claim 6, wherein the neutral amino acid is selected from the group consisting of glycine, alanine and phenylanine.

8. An antiperspirant active composition according to claim 7, wherein the neutral amino acid is glycine.

9. An antiperspirant active composition according to claim 5, wherein the composition has a peak 4 relative area of at least 25% and a peak 3 relative area of less than 50%, the sum of the peak 3 and peak 4 relative areas being at least 40%.

10. An antiperspirant active composition according to claim 9, wherein the composition contains up to 35% peak 1 relative area, and less than 10% peak 2 relative area.

11. An antiperspirant active compositions according to claim 5, wherein 8–18% of the total area under the $^{26}Al$ spectrum from 140 ppm to −80 ppm is contained in a resonance line at 71.5–73.5 ppm.

12. An antiperspirant active composition according to claim 6, wherein 8–18% of the total area under the $^{27}Al$ spectrum from 140 ppm to −80 ppm is contained in a resonance line at 71.5–73.5 ppm.

13. An antiperspirant active composition according to claim 6, wherein the composition has a peak 4 relative area of at least 25% and a peak 3 relative area of less than 50%, the sum of the peak 3 and peak 4 relative areas being at least 40%.

14. An antiperspirant active composition according to claim 13, wherein the composition contains up to 35% peak 1 relative area, and less than 10% peak 2 relative area.

15. An antiperspirant active composition according to claim 5, wherein the at least one other antiperspirant active material has the formula:

$DO_p(OH)_mQ_n$, where p is either 0 or 1; when p=0 then m=0 and n=4, and when p=1 then m+n=2; Q is a halide or X, X having previously been defined; and D is a metal cation selected from the group consisting of Zr, Hf, Ti and Sn.

16. An antiperspirant active composition according to claim 15, wherein a molar ratio of the at least one basic aluminum material to the at least one other antiperspirant active material is 0.3:1 to 6.0:1.

17. An antiperspirant active composition according to claim 5, wherein the at least one other antiperspirant active material is zirconyl hydroxychloride.

18. An antiperspirant active composition according to claim 17, wherein a molar ratio of the at least one basic aluminum material to the at least one other antiperspirant active material is 0.3:1 to 6.0:1.

19. An antiperspirant active composition according to claim 5, wherein a molar ratio of the at least one basic aluminum material to the at least one other antiperspirant active material is 0.3:1 to 6.0:1.

20. An antiperspirant active composition, formed by a process comprising:

(A) providing at least one basic aluminum material having the empirical formula:

$Al_2(OH)_{6-a}X_a$, where $0.5 \leq a \leq 5.0$; and X is a univalent complex oxoanion of nitrogen or a univalent complex oxoanion of a halogen, which forms salts with $Al^{3+}$ in aqueous solution, so that these salts are essentially completely dissociated, which is readily soluble in water with metallic ions in the solution, and which forms conjugate acids that are strong acids, the at least one basic aluminum material being further characterized by:

(a) size exclusion high performance liquid chromatography peaks corresponding to peak 3 and peak 4 of the size exclusion chromatogram produced from a high performance liquid chromatography technique;

(b) a peak 4 relative area of at least 25%, and a peak 3 relative area of less than 60%, the sum of the relative peak 3 and peak 4 areas being at least 50%;

(c) less than 10% chromatographic peaks eluting at shorter retention times than peak 3, corresponding to peaks 1 and 2;

(d) less than 25% of the aluminum being in the form of $Al^b$ polyhydroxyaquoaluminum;

(e) an $^{27}Al$ NMR spectrum wherein 5% to 30% of the total area under the spectrum from 140 ppm to −80 ppm is contained in a resonance line at 71.5–73.5 ppm; and (f) an $^{27}Al$ NMR spectrum in which the area of the 71.5–73.5 ppm resonance line includes more than 50% of the combined areas of the 62.5–63.5 ppm and 71.5–73.5 ppm resonance lines, and (B) mixing said at least one basic aluminum material with
(1) at least one other antiperspirant active material, which is selected from the group consisting of antiperspirant active salts of Zr salts, antiperspirant active Hf salts, antiperspirant active Ti salts and antiperspirant active Sn salts, and (2) a neutral amino acid.

21. An antiperspirant active composition according to claim 20, wherein said at least one basic aluminum material is provided in an aqueous solution and is mixed with said at least one other antiperspirant active material and said neutral amino acid in an aqueous solution, to form a mixture in solution, the mixture in solution being dried to form the antiperspirant active composition.

22. An antiperspirant active composition according to claim 21, wherein the antiperspirant active composition is in a powder form.

23. An antiperspirant active composition according to claim 21, wherein X is $NO_3^-$.

24. An antiperspirant active composition according to claim 20, wherein a molar ratio of the at least one basic aluminum material to the at least one other antiperspirant active material is 0.3:1 to 6.0:1.

25. An antiperspirant active composition according to claim 20, wherein the at least one other antiperspirant active material has the formula:

$$DO_p(OH)_mQ_n,$$

where p is either 0 or 1; when p=0 then m=0 and n=4, and when p=1 then m+n=2; Q is a halide or X, X having previously been defined; and D is a metal cation selected from the group consisting of Zr, Hf, Ti and Sn.

26. An antiperspirant active composition according to claim 25, wherein a molar ratio of the at least one basic aluminum material to the at least one other antiperspirant active material is 0.3:1 to 6.0:1.

27. An antiperspirant active composition according to claim 20, wherein the at least one other antiperspirant active material is zirconyl hydroxychloride.

28. An antiperspirant active composition according to claim 27, wherein a molar ratio of the at least one basic aluminum material to the at least one other antiperspirant active material is 0.3:1 to 6.0:1.

29. A process of forming the antiperspirant active composition according to claim 5, comprising mixing said at least one basic aluminum material, said at least one other antiperspirant active material and said neutral amino acid.

30. The process according to claim 29, wherein the at least one basic aluminum material and the at least one other antiperspirant active material are in respective solutions when mixed.

31. The process according to claim 29, wherein the mixing is performed at room temperature.

* * * * *